(12) United States Patent
Rabhi et al.

(10) Patent No.: US 11,634,452 B2
(45) Date of Patent: Apr. 25, 2023

(54) COMPOUNDS FOR TREATING NEURODEGENERATIVE DISORDERS

(71) Applicants: ETHNODYNE, Paris (FR); CENTRE NATIONAL DE LA RECHERCHE SCIENTIFIQUE (CNRS), Paris (FR)

(72) Inventors: Chérif Rabhi, Bretigny sur Orge (FR); Léon Cariel, Paris (FR); Christian Da Costa Noble, Paris (FR); Jamal Ouazzani, Massy (FR); Guillaume Arcile, Les Ulis (FR); Géraldine Le Goff, Antony (FR)

(73) Assignees: ETHNODYNE, Paris (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 194 days.

(21) Appl. No.: 16/772,121

(22) PCT Filed: Dec. 11, 2017

(86) PCT No.: PCT/IB2017/001757
§ 371 (c)(1),
(2) Date: Jun. 11, 2020

(87) PCT Pub. No.: WO2019/116069
PCT Pub. Date: Jun. 20, 2019

(65) Prior Publication Data
US 2021/0070799 A1   Mar. 11, 2021

(51) Int. Cl.
*C07J 19/00* (2006.01)
*A61P 25/28* (2006.01)
*C07J 41/00* (2006.01)

(52) U.S. Cl.
CPC .......... *C07J 41/0088* (2013.01); *A61P 25/28* (2018.01); *C07J 19/00* (2013.01)

(58) Field of Classification Search
CPC ................ C07J 19/00; C07J 71/001
See application file for complete search history.

(56) References Cited

U.S. PATENT DOCUMENTS

2012/0196815 A1   8/2012   Timmerman et al.

FOREIGN PATENT DOCUMENTS

WO   2015/077780 A1   5/2015

OTHER PUBLICATIONS

Hirayama, M., et al., "Stereoselective Synthesis of Withaferin A and 27-Deoxywithaferin A," Tetrahedron Letters (45):4725-4728, 1982.
International Search Report and Written Opinion dated May 14, 2018, issued in in corresponding Application No. PCT/IB2017/001757, filed Dec. 11, 2017, 12 pages.
Yousuf, S.K., et al., "Ring A Structural Modified Derivatives of Withaferin A and the Evaluation of Their Cytotoxic Potential," Steroids 76(10):1213-1222, May 2011.

*Primary Examiner* — Susanna Moore
(74) *Attorney, Agent, or Firm* — Christensen O'Connor Johnson Kindness PLLC

(57) ABSTRACT

The invention relates to compounds of formula (I), their method of synthesis as well as their use to treat neurodegenerative disorders.

Figure 1A:
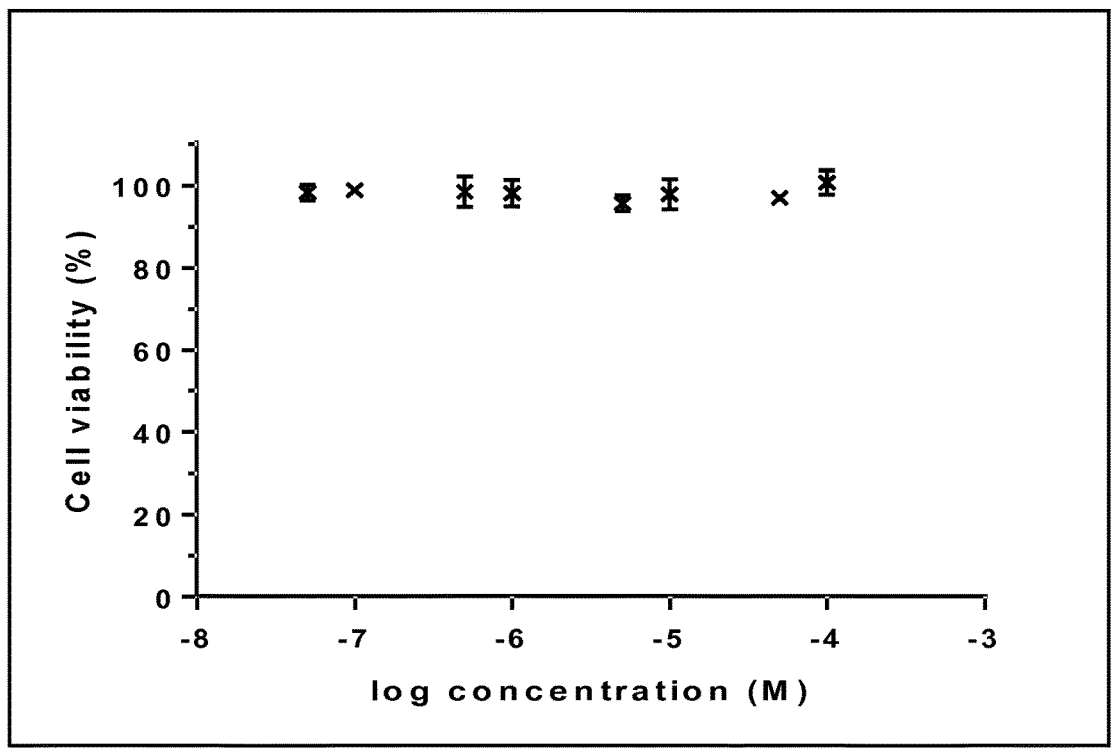

14 Claims, 10 Drawing Sheets a b c d

COMPOUNDS FOR TREATING NEURODEGENERATIVE DISORDERS

The invention relates to compounds of formula (I), their method of synthesis as well as their use to treat neurodegenerative disorders.

Neurodegenerative disorders correspond to the disorders in the central nervous system that are characterized by the progressive loss of neural tissues. Neurodegenerative diseases are one of the most debilitating conditions and usually associated with mutated genes, accumulation of abnormal proteins, increased reactive oxygen species (ROS) or destruction of the neurons in a specific part of the brain. Changes in the neurons cause them to function abnormally and eventually result in the cells' demise. The reason is the inability of the neurons to regenerate on their own after the neural deterioration or severe damage. This leads to disorders like Alzheimer's disease (AD), Parkinson's disease (PD), multiple sclerosis (MS), Amyotrophic lateral sclerosis (ALS) and Motor Neuron Diseases (MND). The incidence is expected to soar as the population ages, because neurodegenerative diseases strike primarily in mid- to late-life.

Multiple sclerosis (MS), also known as disseminated sclerosis or encephalomyelitis disseminata, is an inflammatory disease in which the insulating covers of nerve cells in the brain and spinal cord are damaged. This damage disrupts the ability of parts of the nervous system to communicate, resulting in a wide range of signs and symptoms, including physical, mental, and sometimes psychiatric problems. MS takes several forms, with new symptoms either occurring in isolated attacks (relapsing forms) or building up over time (progressive forms). Between attacks, symptoms may disappear completely. However, permanent neurological problems often occur, especially as the disease advances.

Multiple sclerosis is the most common autoimmune disorder affecting the central nervous system.

The cause of MS is not clear, but its pathology consists of immune infiltration into the central nervous system (CNS), inflammation, demyelination and finally axonal degeneration. MS is usually diagnosed based on the presenting signs and symptoms and the results of supporting medical tests.

Myelination in the CNS involves sequential developmental processes in which precursors of oligodendrocytes (OPCs) migrate, proliferate, and differentiate into newly formed oligodendrocytes (OL), after which those oligodendrocytes selected by target-dependent survival mechanisms wrap myelin membrane around the axons to form the sheath. Each oligodendrocyte can myelinate many axons, with the number of wraps proportional to the axon diameter and regulated tightly by reciprocal signaling between oligodendrocyte and axons.

So far, there is no known cure for multiple sclerosis. Treatments attempt to improve function after an attack and prevent new attacks.

The term α-synucleinopathies is usually employed to define a group of neurodegenerative disorders that show common pathologic proteinaceous accumulation of α-synuclein aggregates. In these diseases, α synuclein aggregates are deposited in selective vulnerable populations of neuronal and glial cells (Goedert M (1999) Philos Trans R Soc Lond B Biol Sci 354:1101-1118; Spillantini M. G & Goedert M (2000) Ann N Y Acad Sci 920:16-27; Trojanowski J. Q & Lee V. M (2003) Ann N Y Acad Sci 991:107-110.).

From a clinical point of view, α-synucleinopathies include symptomatically heterogeneous disorders, among them Lewy bodies-associated diseased such as Parkinson's Disease (PD), dementia with Lewy bodies, also known as Lewy body dementia, diffuse Lewy body disease, cortical Lewy body disease, and senile dementia of Lewy type, multiple system atrophy, Lewy bodies dysphagia as well as neurodegeneration with brain iron accumulation type I and pure autonomic failure. Lewy body disease is one of the most common causes of dementia in the elderly. Dementia is the loss of mental functions severe enough to affect normal activities and relationships.

Alpha-synuclein is a protein of unknown function primarily found in neural tissue, making up as much as 1% of all proteins in the cytosol of brain cells. It is predominantly expressed in the neocortex, hippocampus, substantia nigra, thalamus, and cerebellum. It is a neuronal protein, but can also be found in the neuroglial cells. In the brain, alpha-synuclein is found mainly at the tips of nerve cells (neurons) in specialized structures called presynaptic terminals. Within these structures, alpha-synuclein interacts with phospholipids and proteins. Presynaptic terminals release chemical messengers, called neurotransmitters, from compartments known as synaptic vesicles. The release of neurotransmitters relays signals between neurons and is critical for normal brain function.

Although the function of alpha-synuclein is not well understood, studies suggest that it plays an important role in maintaining a supply of synaptic vesicles in presynaptic terminals. It may also help regulate the release of dopamine, a type of neurotransmitter that is critical for controlling the start and stop of voluntary and involuntary movements.

Alpha-synuclein is specifically upregulated in a discrete population of presynaptic terminals of the brain during a period of acquisition-related synaptic rearrangement. Apparently, alpha-synuclein is essential for normal development of the cognitive functions. Knock-out mice with the targeted inactivation of the expression of alpha-synuclein show impaired spatial learning and working memory.

Parkinson's disease (PD) is the second most common neurodegenerative disorder in the United States.

The predominant motor symptoms of PD including slow movement, resting tremor, rigidity and gait disturbance are caused by the loss of dopaminergic neurons in the substantia nigra (SN).

Cognitive dysfunction in PD is a prominent non-motor symptom, highly contributing to morbidity and mortality in this disease. The etiologies of cognitive impairments in PD patients are heterogenous and include executive dysfunctions, thought disorders, and very often manifest in dementia, which affects up to 80% of patients.

Current pharmaceutical treatments for Parkinson's disease focus on dopaminergic agents, which either mimic dopamine, or increase levels of dopamine in the body. The most common therapy is levodopa, which is a metabolic precursor of dopamine. However, long term levodopa therapy is often accompanied by dyskinesias, which are sudden, involuntary movements.

Amyloidosis refers to a pathological condition characterized by the presence of amyloid fibrils. Amyloid is a generic term referring to a group of diverse but specific protein deposits (intracellular or extracellular) which are seen in a number of different diseases. Though diverse in their occurrence, all amyloid deposits have common morphologic properties. They also share common ultrastructural features and common X-ray diffraction and infrared spectra. Amyloid-related diseases can either be restricted to one organ or spread to several organs. Once these amyloids have formed, there is no known, widely accepted therapy or treatment which significantly dissolves amyloid deposits in situ, prevents further amyloid deposition or prevents the initiation of amyloid deposition.

Alzheimer's disease (AD) is a degenerative central nervous system disorder associated with extensive loss of specific neuronal cells, and characterized clinically by progressive loss of memory, cognition, reasoning, judgment and emotional stability that gradually leads to profound mental deterioration and ultimately death. People suffering from Alzheimer's disease develop a progressive dementia in adulthood, accompanied by three main structural changes in the brain: diffuse loss of neurons in multiple parts of the brain; accumulation of intracellular protein deposits termed neurofibrillary tangles; and accumulation of extracellular protein deposits termed amyloid or senile plaques, surrounded by misshapen nerve terminals and activated microglia. To date, there is no treatment that stops or reverses the disease and it presently causes up to 100,000 deaths annually.

AD is indeed characterized by excessive production of small hydrophobic peptides called amyloid beta peptides (Aβ peptides) with Aβ42 peptide being particularly neurotoxic leading to pathogenesis of this disease. In specific cases, amyloid fibrils, once deposited, can become toxic to the surrounding cells. For example, these fibrils organized as senile plaques have been shown to be associated with dead neuronal cells, dystrophic neurites, astrocytosis, and microgliosis in patients with AD. According to the dominant scientific hypothesis for AD, called amyloid cascade or amyloid hypothesis, it is believed that progressive cerebral deposition of particular amyloidogenic peptides, beta-amyloid peptides (Aβ peptides), play a detrimental role in the pathogenesis of AD and can precede cognitive symptoms and onset of dementia by years or possibly even decades (Hardy J, & Selkoe D J, Science. (2002) 297 (5580): 353-6).

Thus prevention of production of these peptides has become the major focus of pharmaceutical industry approaches to treatment of AD. The Aβ peptides are produced as a result of excessive processing of the amyloid precursor protein (APP), the parent trans-membrane protein found in neurons and other cells (Selkoe, D J. Trends Cell Biol. 1998, 8(11):447-53). Amyloid plaques are composed primarily of 40 and 42 amino acid peptides (called Aβ40 and Aβ42, respectively) derived from amyloid precursor protein (APP) by sequential proteolysis catalyzed by the aspartyl protease, beta-secretase, followed by presenilin-dependent gamma-secretase cleavage. Aβ42 is more prone to aggregation and deposition and therefore the cause of neurotoxicity as well as synaptic loss (Callizot N, et al., 2013. J Neurosci Res. 91: 706-16).

The mechanism by which Aβ peptides induce the neuronal cell death is not clear. However, numerous mechanisms such as intracellular calcium accumulation, reactive oxygen species (ROS) and nitric oxide (NO) productions, alteration of the cytoskeleton and nucleus and inflammatory processes that converge to the ubiquitous pathways of necrosis or apoptosis have been proposed. Since the AD brain is characterized by an ongoing chronic inflammatory process, research is directed at finding the root of this inflammatory response. Neurofibrillary tangles and senile plaques (aggregates mainly formed by amyloid beta peptide) are two landmark lesions in Alzheimer's disease. It has been documented that these oligomeric forms of Aβ interact with receptors from the glutamatergic system such as the NMDA-receptors, which are responsible for maintaining glutamate homeostasis (Campos-Peña. V. & M. A. Meraz-Rios, 2014 Neurochemistry, Dr. Thomas Heinbockel (Ed.), ISBN: 978-953-51-1237-2, InTech, DOI: 10.5772/57367).

In this view, an early pharmacological treatment with substances reducing the glutamate overstimulation might represent a very good option for the treatment of patients with AD. Present therapies treat one or more symptoms of AD, including memory loss that disrupts daily life; challenges in planning or solving problems, difficulty completing familiar tasks at home, at work or at leisure, confusion with time or place, trouble understanding visual images and spatial relationships, new problems with words in speaking or writing, misplacing things and losing the ability to retrace steps, decreased or poor judgment, withdrawal from work or social activities, changes in mood and personality.

Another type of amyloidosis is cerebral amyloid angiopathy (CAA). CAA is the specific deposition of amyloid-P fibrils in the walls of leptomingeal and cortical arteries, arterioles and veins. It is commonly associated with AD, Down's syndrome and normal aging, as well as with a variety of familial conditions related to stroke or dementia (Frangione et al., Amyloid: J. Protein Folding Disord. 8, Suppl. 1, 36-42 (2001)).

Presently available therapies for treatment of amyloid diseases are almost entirely symptomatic, and no comprehensive pharmacological therapy is currently available for the prevention or treatment of, for example, Alzheimer's disease (Roberson, E. D. & Mucke, L. (2006). Science, 314, 781-784).

Studies have shown a correlation between soluble AB levels and the extent of synaptic loss/severity of cognitive impairment (Mucke, L., et al., (2000) J Neurosci; 20:4050). Therefore, any substances reducing AB neurotoxicity may be useful as a new therapeutic agent for the treatment or prevention of amyloid-related diseases and in particular AD.

Motor neuron diseases or disorders (MNDs) are characterized by progressive loss of motor neurons of the spinal cord ('lower motor neurons' (MN)) or motor neurons of the brain ('upper motor neurons'), or both, leading to atrophy and/or spasticity of the associated musculature. Spinal muscular atrophy (SMA), amyotrophic lateral sclerosis (ALS) and hereditary spastic paraplegia (HSP) are the most common MNDs.

When there are disruptions in the signals between the upper motor neurons and the lower motor neurons, the limb muscles develop stiffness (spasticity), movements become slow and effortful, and tendon reflexes such as knee and ankle jerks become overactive. Over time, the ability to control voluntary movements (such as speaking, walking, breathing, and swallowing) can be lost.

MNDs occur in adults and children. In children, particularly in inherited or familial forms of the disease, symptoms can be present at birth or appear before the child learns to walk. In adults, MNDs occur more commonly in men than in women, with symptoms appearing after age 40.

MNDs are classified according to whether they are inherited or sporadic, and to whether degeneration affects upper motor neurons, lower motor neurons, or both. The causes of most MNDs are not known.

Amyotrophic lateral sclerosis (ALS), also called Lou Gehrig's disease or classical motor neuron disease, is the most common form of MND, with both upper and lower motor neuron involvement. ALS affects both upper and lower motor neurons. It has inherited and sporadic forms and can affect the arms, legs, or facial muscles. Although the majority of ALS cases are sporadic, up to 10% are inherited (Robberecht & Philips, 2013) and the most common familial forms of ALS in adults are caused by mutations of the superoxide dismutase gene, or SOD1, located on chromosome 21. There are also rare juvenile-onset forms of familial ALS. This form of the disease is characterized by weakness and wasting in the limbs. Muscle weakness and atrophy occur on both sides of the body. Affected individuals lose strength and the ability to move their arms and legs, and to hold the body upright. Other symptoms include spasticity, spasms, muscle cramps, and fasciculations. Speech can become slurred or nasal. When muscles of the diaphragm and chest wall fail to function properly, individuals lose the ability to breathe without mechanical support. Although the disease does not usually impair a person's mind or personality, several recent studies suggest that some people with ALS may develop cognitive problems involving word fluency, decision-making, and memory. Most individuals with ALS die from respiratory failure, usually within 3 to 5 years from the onset of symptoms.

Progressive bulbar palsy (PBP) involves both the upper and lower motor neurons. Symptoms include pharyngeal muscle weakness (involved with swallowing), weak jaw and facial muscles, progressive loss of speech, and tongue muscle atrophy. Limb weakness with both lower and upper motor neuron signs is almost always evident but less prominent. Affected persons have outbursts of laughing or crying (called emotional lability). In about 25% of individuals with ALS, early symptoms begin with bulbar involvement. Some 75% of individuals with classic ALS eventually show some bulbar involvement. Life expectancy is between six months and three years from onset of symptoms.

Progressive muscular atrophy (PMA) affects only a small proportion of people, mainly causing damage to the lower motor neurons. Early symptoms may be noticed as weakness or clumsiness of the hand. Most people live for more than five years.

Primary lateral sclerosis (PLS) is a rare form of MND involving the upper motor neurons only, causing mainly weakness in the lower limbs, although some people may experience clumsiness in the hands or speech problems. It occurs when specific nerve cells in the motor regions of the cerebral cortex gradually degenerate, causing the movements to be slow and effortful. Difficulty with balance may lead to falls. PLS is more common in men than in women, with a very gradual onset that generally occurs between ages 40 and 60. The cause is unknown. The symptoms progress gradually over years, leading to progressive stiffness and clumsiness of the affected muscles. The disorder is not fatal but may affect quality of life, if it develops into ALS.

Spinal muscular atrophy (SMA) is an autosomal, hereditary recessive disorder caused by defects in the gene SMN1. In SMA, insufficient levels of the SMN protein lead to degeneration of the lower motor neurons, producing weakness and wasting of the skeletal muscles. This weakness is often more severe in the trunk and upper leg and arm muscles than in muscles of the hands and feet.

Kennedy's Disease, also known as progressive spinobulbar muscular atrophy, is an X-linked recessive progressive disorder of the motor neurons caused by mutations in the gene for the androgen receptor. Symptoms include weakness and atrophy of the facial, jaw, and tongue muscles, leading to problems with chewing, swallowing, and changes in speech. Early symptoms may include muscle pain and fatigue. Individuals with Kennedy's disease also develop sensory loss in the feet and hands. It only affects men, but women may carry the mutation. The course of the disorder is generally slowly progressive. Individuals tend to remain ambulatory until late in the disease. The life expectancy for individuals with Kennedy disease is usually normal.

Post-polio syndrome (PPS) is a condition that can strike polio survivors decades after their recovery from poliomyelitis. Polio is an acute viral disease that destroys motor neurons. PPS and Post-Polio Muscular Atrophy (PPMA) are thought to occur when the surviving motor neurons are lost in the aging process or through injury or illness. Symptoms include fatigue, slowly progressive muscle weakness, muscle atrophy, fasciculations, cold intolerance, and muscle and joint pain. These symptoms appear most often among muscle groups affected by the initial disease, and may consist of difficulty breathing, swallowing, or sleeping. PPS is not usually life threatening. Doctors estimate that 25 to 50 percent of survivors of paralytic poliomyelitis usually develop PPS.

Multifocal motor neuropathy (MMN) is a progressively worsening condition where muscles in the extremities gradually weaken. MMN is thought to be autoimmune and involves only lower motor nerves. MMN usually involves very little pain however muscle cramps, spasms and twitches can cause pain for some sufferers. MMN is not fatal, and does not diminish life expectation.

Monomelic amyotrophy (MMA) is an untreatable, focal motor neuron disease that primarily affects young males in India and Japan. MMA is marked by insidious onset of muscular atrophy, which stabilizes at a plateau after two to five years from which it neither improves nor worsens.

Paraneoplastic motor neuron disease is a disease affecting the motor neurons.

Lambert-Eaton Myasthenic Syndrome (LEMS) is a rare autoimmune disorder characterized by muscle weakness of the limbs. Around 60% of those with LEMS have an underlying malignancy, most commonly small cell lung cancer; it is therefore regarded as a paraneoplastic syndrome.

Myasthenia gravis (MG) leads to fluctuating muscle weakness and fatigue. In the most common cases, muscle weakness is caused by circulating antibodies that block acetylcholine receptors at the postsynaptic neuromuscular junction, inhibiting the excitatory effects of the neurotransmitter acetylcholine on nicotinic receptors at neuromuscular junctions. Alternatively, in a much rarer form, muscle weakness is caused by a genetic inherited defect in some portion of the neuromuscular junction.

Botulism, a rare and potentially fatal illness caused by a toxin produced by the bacterium *Clostridium botulinum*, prevents muscle contraction by blocking the release of acetyl choline, thereby halting postsynaptic activity of the neuromuscular junction.

Hereditary spastic paraplegia (HSP) is the collective term for a group of clinically and genetically heterogeneous neurodegenerative disorders characterized by progressive spasticity and weakness in the lower limbs due to loss of upper motor neurons (Harding, 1983).

There is no cure or standard treatment for the MNDs. Symptomatic and supportive treatment can help people be more comfortable while maintaining their quality of life. Research has provided evidence about the role of excitotoxicity in the pathophysiology of sporadic amyotrophic lateral sclerosis and suggests that glutamate receptors activation contributes greatly in mediating injury to motor neurons.

Thus, there is a clear need for alternative therapies that prevent progression and hopefully reverse the effects of neurodegenerative diseases on human.

Surprisingly, the applicant has found that, by using a specific compound, it is possible to treat neurodegenerative disorders.

The purpose of the invention is therefore to use a compound of formula (I)

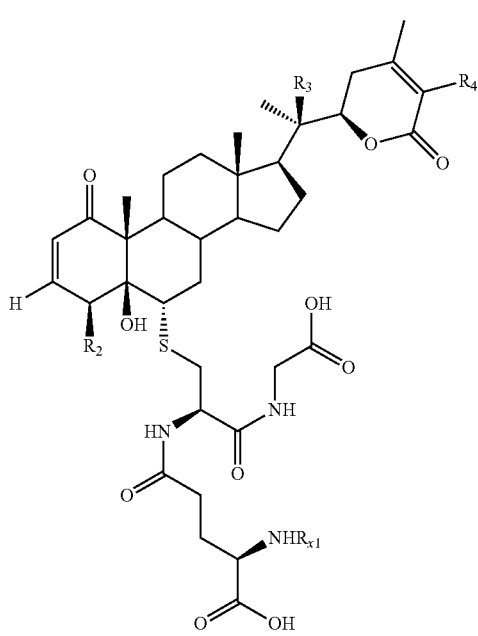

(I)

in which
R2 is H, OH, an heteroatom, $(CH_2)n-CH_3$, with n=2, 4 or 6, a glucopyranose or a glucofuranose;
R3 is H, OH, $CH_2OH$ or a glucofuranose;
R4 is H, OH, $CH_3$, $CH_2OH$, a glucofuranose, $C_6H_5$, $C_{10}H_7$, $C_6H_4X$ or $C_{10}H_6X$ with X=F, Cl, Br or I;
$R_{X1}$ is H or an aminoacid chosen among tryptophane, lysine, methionine, phenylalanine, threonine, valine, leucine, isoleucine, arginine or histidine for the treatment or prevention of neurodegenerative disorders. The invention is also relative to the synthesis of this compound.

Figure 1B:
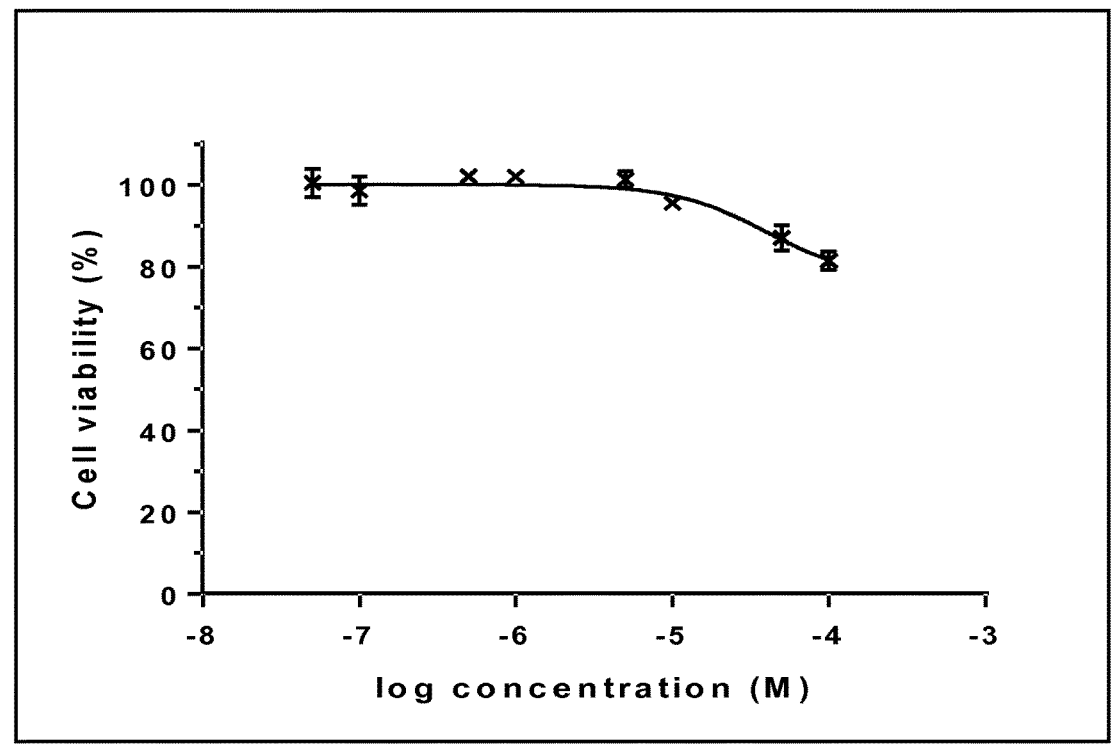
Figure 1C:
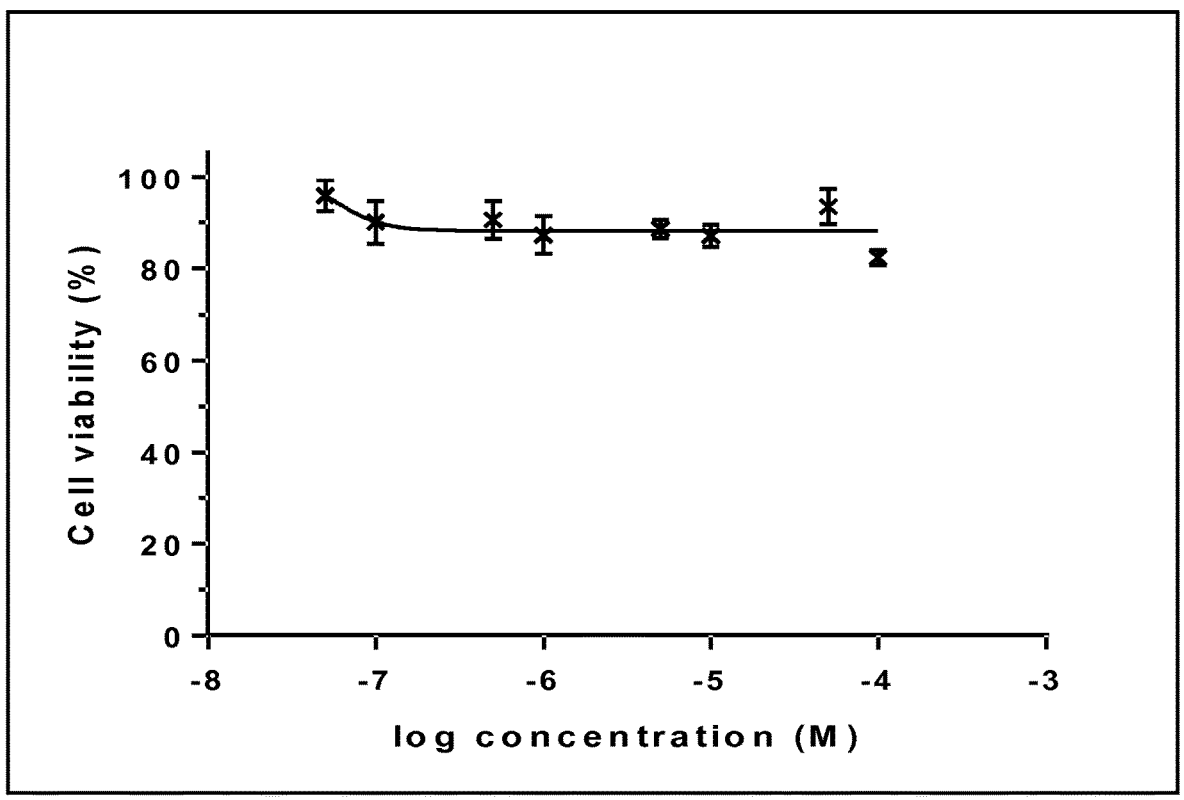

Other objects, features, aspects and advantages of the invention will appear more clearly on reading the description and examples that follow:

FIG. 1: cytotoxicity tests with compound CR777 on several cell lines. a=MRC5, b=HCT116, c=HUVEC.

Figure 2:
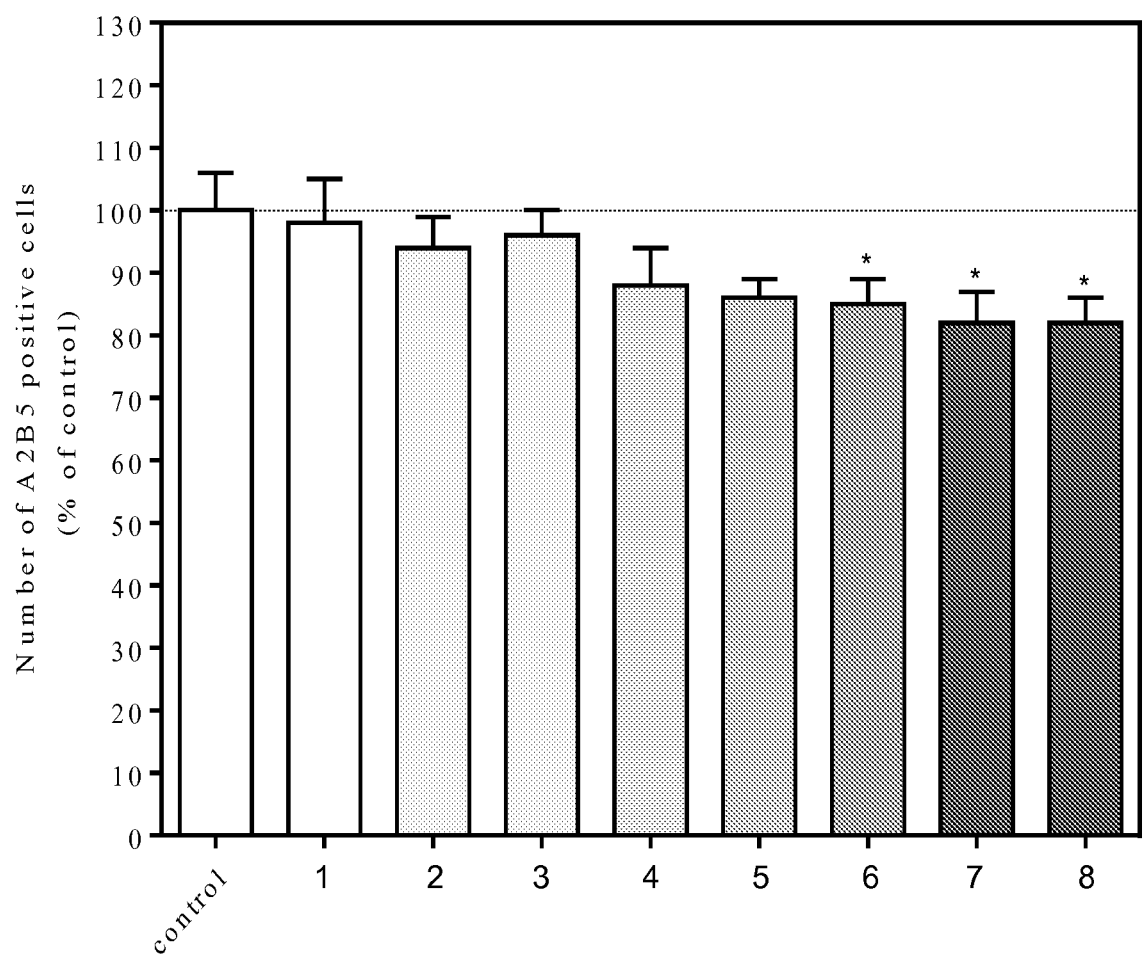

FIG. 2: Effect of CR777 on OPC number after 12 days of treatment. Bar 1: CR777 1 pmol/L, bar 2: CR777 10 pmol/L, bar 3: CR777 100 pmol/L, bar 4: CR777 1 nmol/L, bar 5: CR777 10 nmol/L, bar 6: CR777 100 nmol/L, bar 7: CR777 1 μmol/L, bar 8: CR777 10 μmol/L. Data were expressed as percentage of control as mean+/−SEM (100%=no compound). Statistical analyses were performed using the Graph pad prism for one-way ANOVA followed by PLSD fisher's test. *p<0.05 was considered significant.

Figure 3:
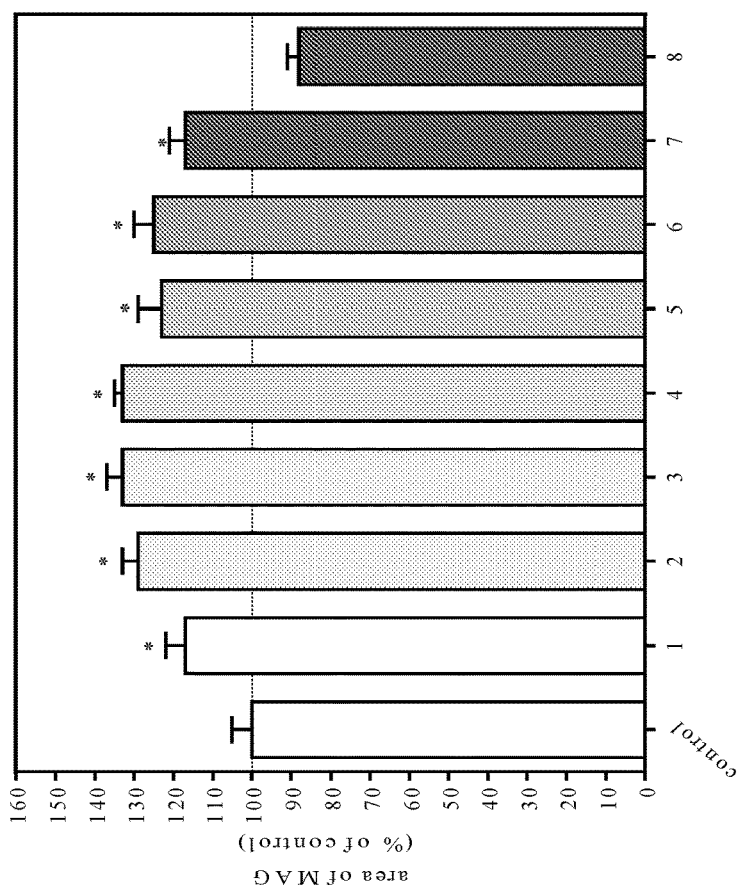
Figure 3:
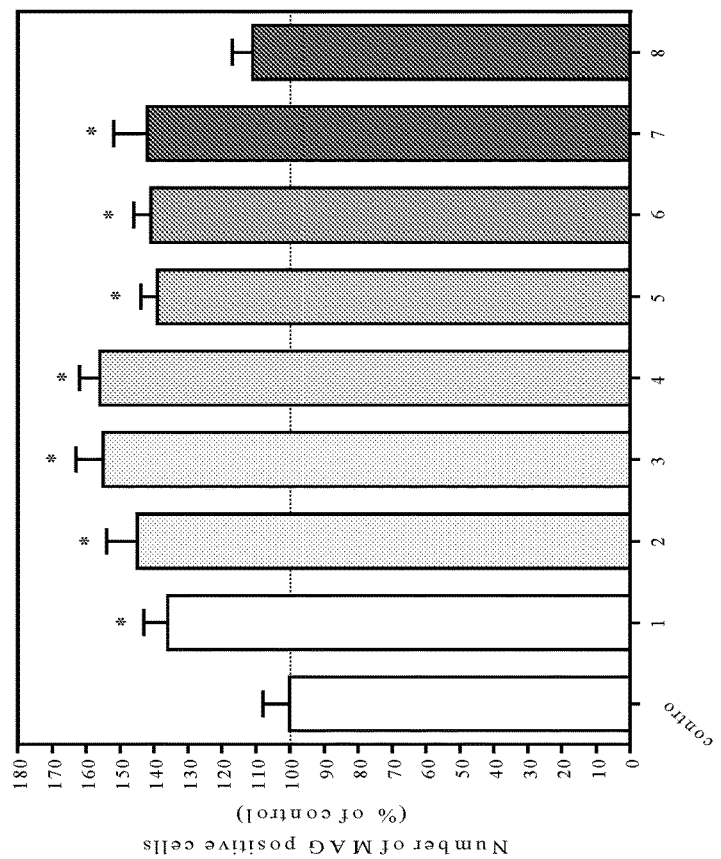

FIG. 3: Effect of CR777 on a) the number of MAG positive cells (OL) and b) the area of MAG expression after 18 days of treatment. Bar 1: CR777 1 pmol/L, bar 2: CR777 10 pmol/L, bar 3: CR777 100 pmol/L, bar 4: CR777 1 nmol/L, bar 5: CR777 10 nmol/L, bar 6: CR777 100 nmol/L, bar 7: CR777 1 μmol/L, bar 8: CR777 10 μmol/L. Data were expressed as percentage of control as mean±SEM (100%=no compound). Statistical analyses were performed using the Graph pad prism for one-way ANOVA followed by PLSD fisher's test. *p<0.05 was considered significant.

Figure 4:
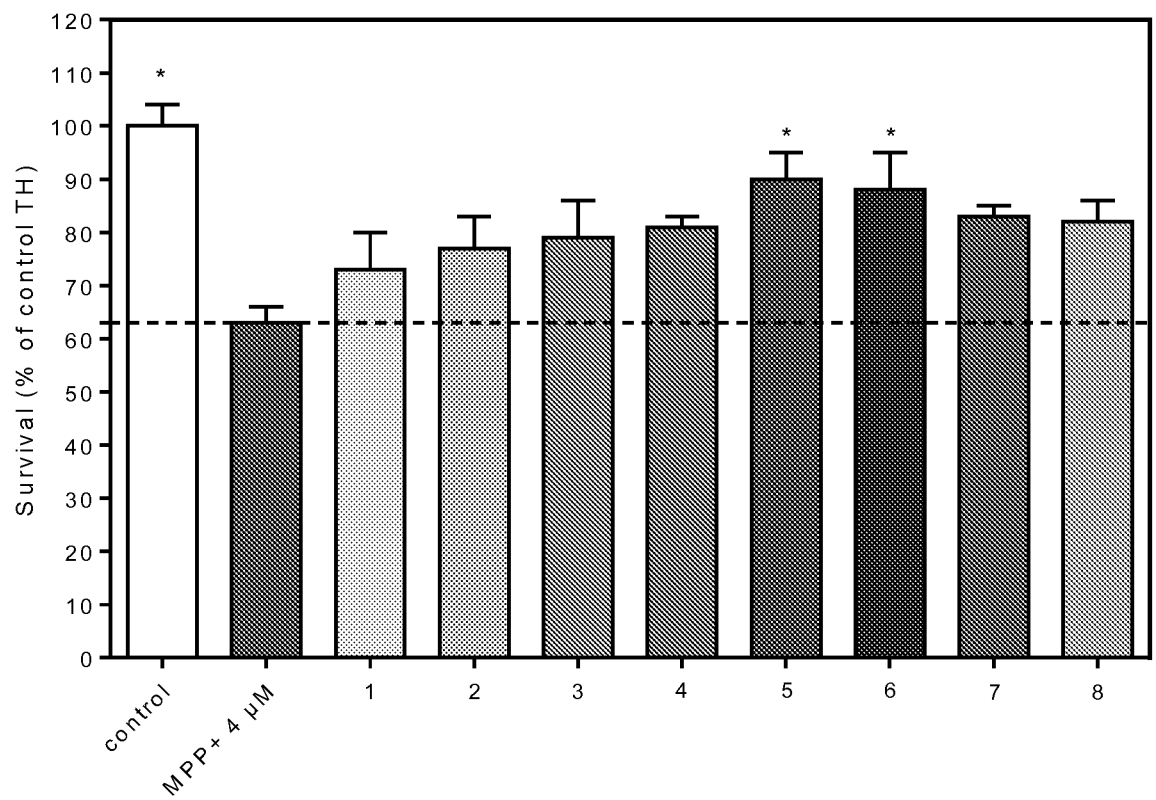

FIG. 4: Effect of CR777 on neuron survival of primary rat dopaminergic neurons (TH positive neurons) injured with MPP+ (48 h, 4 μM). Bar 1: CR777 1 pmol/L, bar 2: CR777 10 pmol/L, bar 3: CR777 100 pmol/L, bar 4: CR777 1 nmol/L, bar 5: CR777 10 nmol/L, bar 6: CR777 100 nmol/L, bar 7: CR777 1 μmol/L, bar 8: CR777 10 μmol/L. Data were expressed as percentage of control as mean±SEM (100%=no MPP+, no compound). Statistical analyses were performed using the Graph pad prism for one-way ANOVA followed by Dunnett's test. *p<0.05 was considered significant (vs MPP+ condition).

Figure 5:
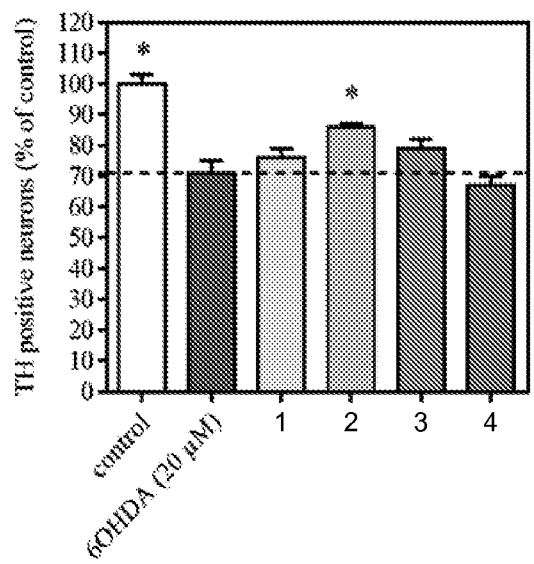

FIG. 5: Effect of CR777 on neuron survival of primary rat dopaminergic neurons (TH positive neurons) injured with 6-OHDA (48 h, 200$ $). Bar 1: CR777 1 nmol/L, bar 2: CR777 10 nmol/L, bar 3: CR777 100 nmol/L, bar 4: CR777 1 μmol/L. Data were expressed as percentage of control as mean±SEM (100%=no MPP+, no compound). Statistical analyses were performed using the Graph pad prism for one-way ANOVA followed by PLSD Fisher's test. *p<0.05 was considered significant.

Figure 6:
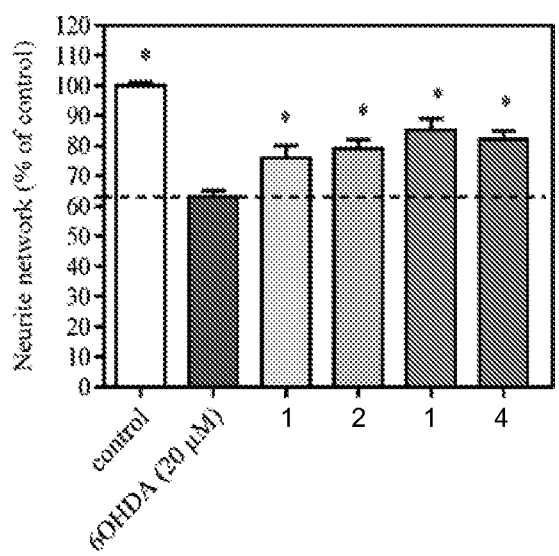

FIG. 6: Effect of CR777 on neurite network of primary rat dopaminergic neurons (TH positive neurons) injured with 6-OHDA (48 h, 200$ $). Bar 1: CR777 1 nmol/L, bar 2: CR777 10 nmol/L, bar 3: CR777 100 nmol/L, bar 4: CR777 1 μmol/L. Data were expressed as percentage of control as mean±SEM (100%=no MPP+, no compound). Statistical analyses were performed using the Graph pad prism for one-way ANOVA followed by PLSD Fisher's test. *p<0.05 was considered significant.

Figure 7:
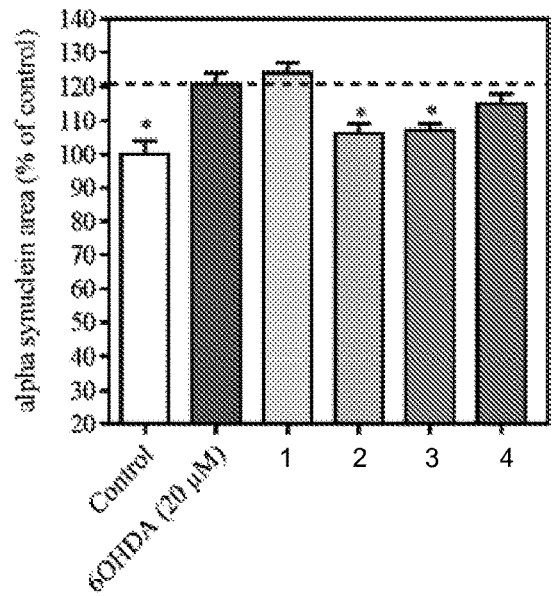

FIG. 7: Effect of CR777 on α-syn aggregation of primary rat dopaminergic neurons (TH positive neurons) injured with 6-OHDA (48 h, 200$ $). Bar 1: CR777 1 nmol/L, bar 2: CR777 10 nmol/L, bar 3: CR777 100 nmol/L, bar 4: CR777 1 μmol/L. Data were expressed as percentage of control as mean±SEM (100%=no MPP+, no compound). Statistical analyses were performed using the Graph pad prism for one-way ANOVA followed by PLSD Fisher's test. *p<0.05 was considered significant.

Figure 8:
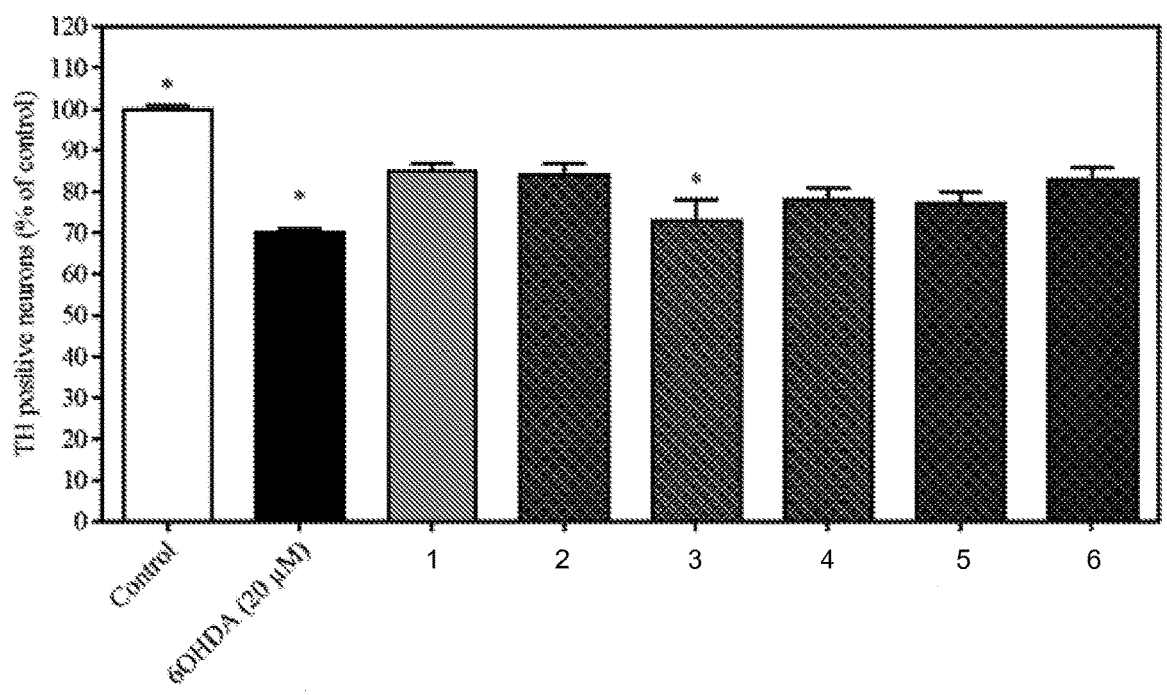

FIG. 8: Neuroprotective effect of CR777 on primary TH positive neuron survival injured with 6-OHDA (20 μM, 48 h) in presence or absence of inhibitors. Bar 1: 6-OHDA (20 μM)+CR777 10 nM+FTS (4 μM), bar 2: CR777 10 nM+BEZ235 (40 nM), bar 3: CR777 10 nM+L-NAME (100 μM), bar 4: CR777 10 nM+T0070907 (1 μM), bar 5: CR777 10 nM+ABT 199 (5 μM). Data were expressed as percentage of control as mean±SEM (100%=no 6-OHDA, no compound). Statistical analyses were performed using the Graph pad prism for one-way ANOVA followed by PLSD fisher's test. p<0.05 was considered significant.

Figure 9:
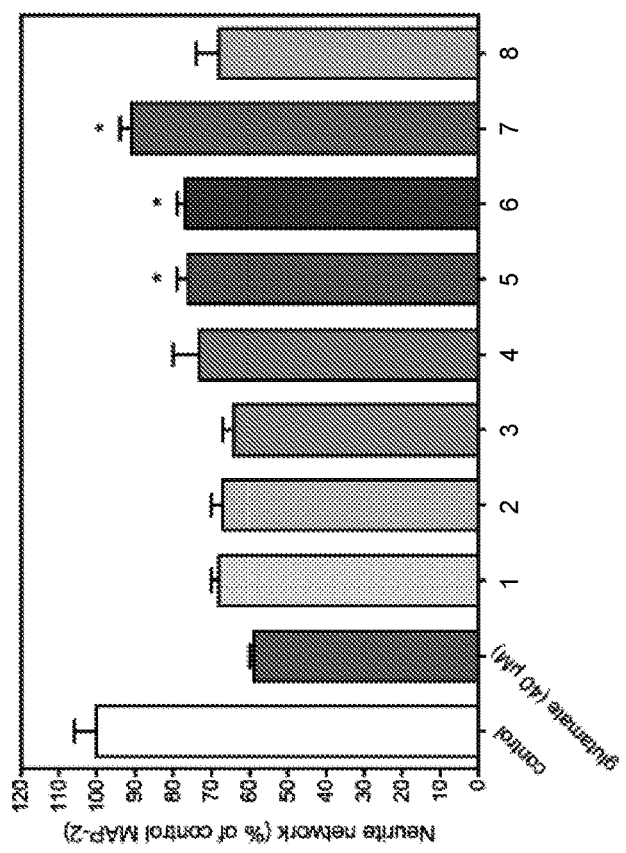
Figure 9:
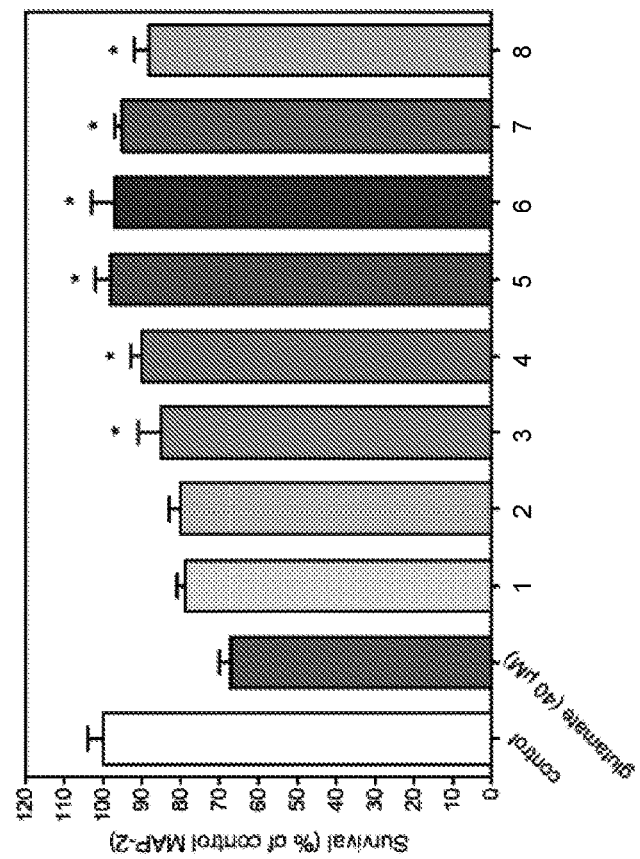

FIG. 9: Effect of CR777 on a) neuron survival and b) neurite network of primary rat cortical neurons injured with glutamate (20 min, 40 μM). Bar 1: CR777 1 pmol/L, bar 2: CR777 10 pmol/L, bar 3: CR777 100 pmol/L, bar 4: CR777 1 nmol/L, bar 5: CR777 10 nmol/L, bar 6: CR777 100 nmol/L, bar 7: CR777 1 μmol/L, bar 8: CR777 10 μmol/L Data were expressed as percentage of control as mean±SEM (100%=no glutamate, no compound). Statistical analyses were performed using the Graph pad prism for one-way ANOVA followed by Dunnett's test. *p<0.05 was considered significant.

Figure 10:
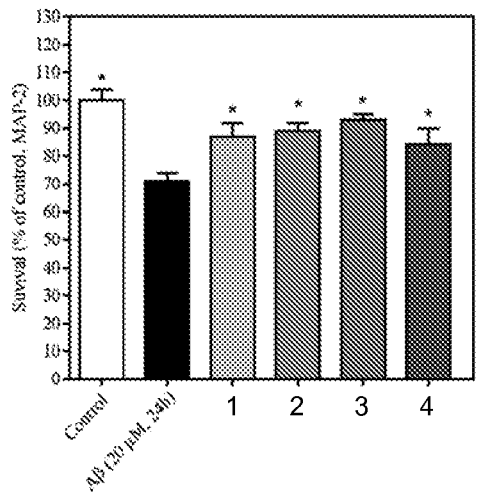
Figure 10:
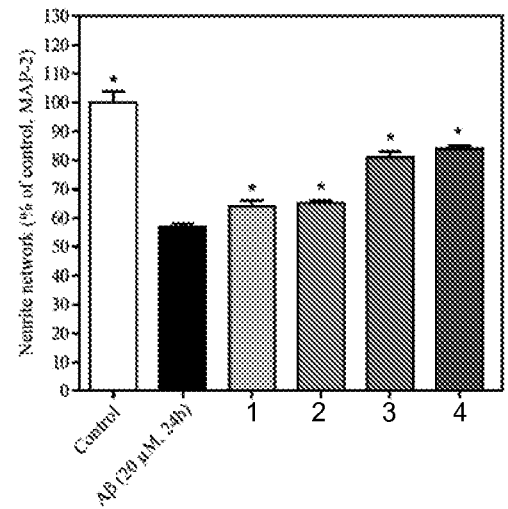
Figure 10:
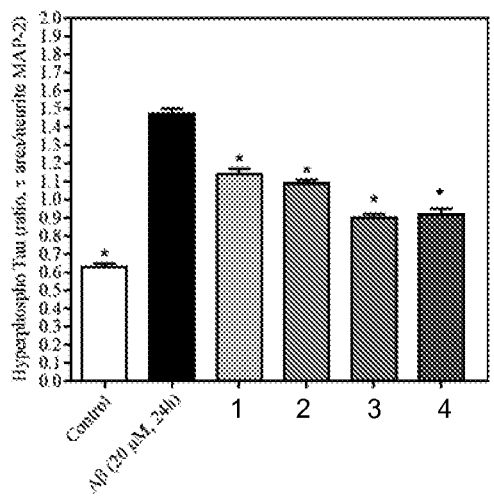
Figure 10:
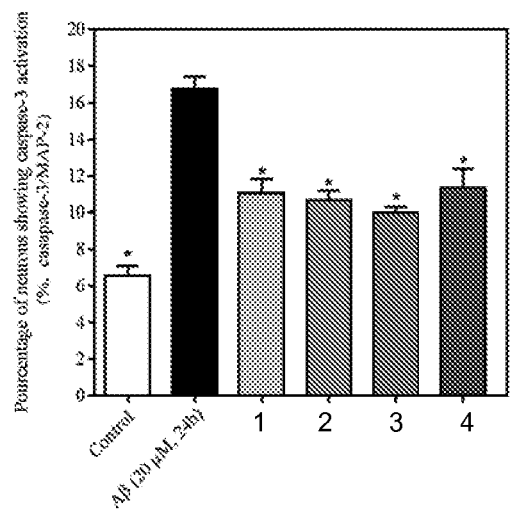

FIG. 10: Effect of CR777 on a) survival b) neurite network c) hyperphosphorylation of tau d) caspase 3 activation of primary rat cortical neurons injured with Aβ1-42 (24 h, 20 μL). Bar 1: 1 nmol/L, bar 2: CR777 10 nmol/L, bar 3: CR777 100 nmol/L, bar 4: CR777 1 μmol/L. Data were expressed as percentage of control as mean±SEM (100%=no injury, no compound). Statistical analyses were performed using the Graph pad prism for one-way ANOVA followed by PLSD Fisher's test. *p<0.05 was considered significant FIG. 11: Effect of CR777 on neuron survival of primary rat motor neurons injured with glutamate (48 h, 5 µM). Bar 1: CR777 1 pmol/L, bar 2: CR777 10 pmol/L, bar 3: CR777 100 pmol/L, bar 4: CR777 1 nmol/L, bar 5: CR777 10 nmol/L, bar 6: CR777 100 nmol/L, bar 7: CR777 1 µmol/L, bar 8: CR777 10 µmol/L. Data were expressed as percentage of control as mean±SEM (100%=no glutamate, no compound). Statistical analyses were performed using the Graph pad prism for one-way ANOVA followed by PLSD fisher's test. *p<0.05 was considered significant.

The invention is directed to a compound of formula (I)

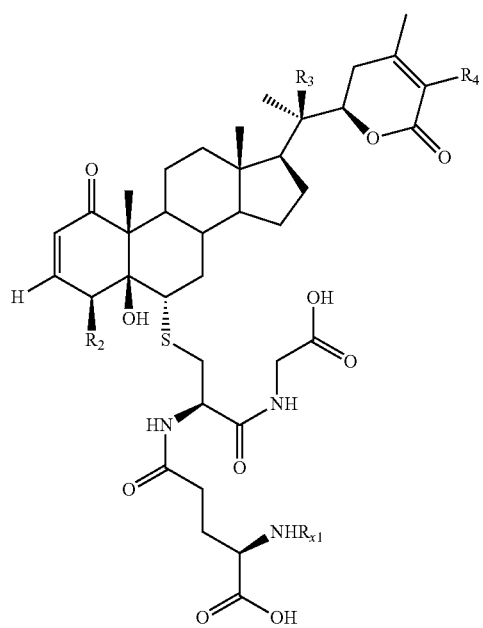

(I)

in which $R_2$ is H, OH, an heteroatom, $(CH_2)n-CH_3$, with n=2, 4 or 6, a glucopyranose or a glucofuranose;

$R_3$ is H, OH, $CH_2OH$ or a glucofuranose;

$R_4$ is H, OH, $CH_3$, $CH_2OH$, a glucofuranose, $C_6H_5$, $C_{10}H_7$, $C_6H_4X$ or $C_{10}H_6X$ with X=F, Cl, Br or I;

$R_{X1}$ is H or an aminoacid chosen among tryptophane, lysine, methionine, phenylalanine, threonine, valine, leucine, isoleucine, arginine or histidine as well as its use for the treatment of neurodegenerative disorders in a mammal. Preferably, the mammal is a human.

Preferably, the heteroatom is chosen among F, Cl, Br and I.

Preferably in the compound of formula (I), the glucopyranose and the glucofructose are D glucopyranose and D glucofructose.

Preferably, in the compound of formula (I), $R_2$ is H, OH or a heteroatom; $R_3$ is H, OH or $CH_2OH$; $R_4$ is H, OH, $CH_3$, $CH_2OH$ and $R_{X1}$ is H or an aminoacid chosen among tryptophane, lysine, methionine, phenylalanine, threonine, valine, leucine, isoleucine, arginine or histidine.

More preferably, in the compound of formula (I), $R_2$ is OH, $R_3$ is H, $R_4$ is $CH_2OH$ and $R_{X1}$ is H, giving the compound CR777 of formula:

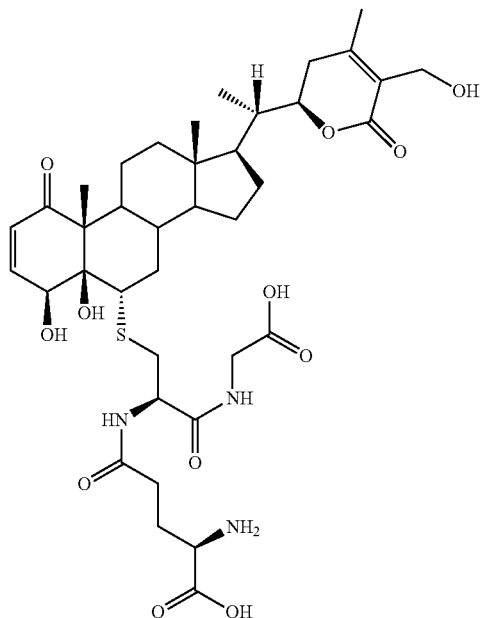

compound CR777

The method of synthesis of the compound of formula (I) comprises two successive stages (a1) and (a2), (a1) being the reaction between a compound of formula (II) in which the substituent R1 is H, OH, an heteroatom or $(CH_2)n-CH3$, with n=2, 4 or 6 and R2, R3, R4 have the same meaning as in formula (I),

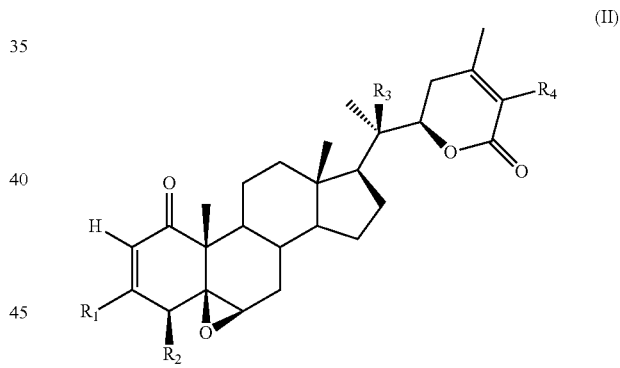

(II)

and a compound of formula (III) in which the substituent $R_{X1}$ has the same meaning as in formula (I)

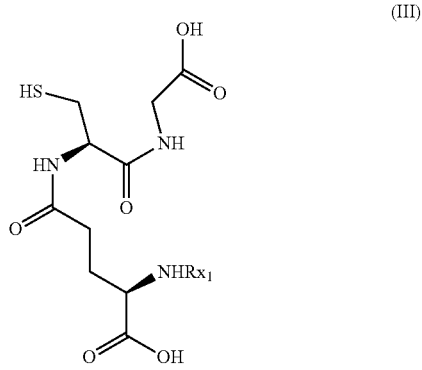

(III)

to obtain the compound of formula (IV), in which R2, R3, R4 and $R_{X1}$ have the same meaning as in formula (I),

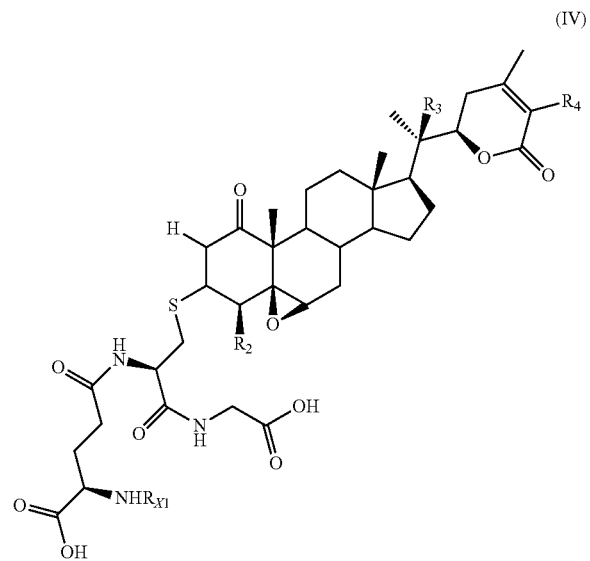

(b1) the reaction between the compound of formula (IV) with the compound of formula (III) to obtain the compound of formula (I).

Preferably, the stages (a1) and (a2) of this synthesis are performed in the presence of at least a solvent. Preferably, the solvent used is tetrahydrofurane and/or water. More preferably, the solvent is a mixture of tetrahydrofurane and water.

Preferably, the stages (a1) and (a2) are performed at a temperature comprised between 40 and 80° C. More preferably, the temperature during the two stages is 65° C. Preferably, the stages (a1) and (a2) last from 6 h to 12 h each.

The compounds of formula (I) according to the invention are useful as medicament.

The compounds of formula (I) can be used to treat or prevent neurodegenerative disorders in a mammal, preferably a human This compound of formula (I) can be used to treat or prevent amyloid-related diseases in a mammal, preferably a human.

Preferably, the amyloid-related diseases comprise Alzheimer's disease, cerebral amyloid angiopathy, inclusion body myositis or Down's syndrome.

In certain embodiments of the invention, the methods and compounds of the invention reduce the progression of AD in particular, and in some embodiments the methods and compositions of the invention are effective to treat a larger spectrum of AD patients. In certain cases the invention is effective for individuals having early onset or familial AD.

The use of the compound of the invention causes in an Alzheimer's patient a stabilization of cognitive function, prevention of a further decline in cognitive function, or prevention, slowing, or stopping of disease progression.

In other embodiment, is described a method of treating or preventing an amyloid-related disease in a subject, preferably a human, comprising administering to a subject a therapeutic amount of a compound of formula (I). Preferably, the amyloid-related disease is Alzheimer's disease, cerebral amyloid angiopathy, inclusion body myositis, macular degeneration, or Down's syndrome. In the method of the invention, the use of compound of formula (I) reduces or inhibits the formation or deposition, neurodegeneration or cellular toxicity of amyloid fibril.

The compound of formula (I) according to the invention can be used to treat or limit development of demyelinating diseases in a mammal, preferably a human.

Preferably, the demyelinating diseases comprise multiple sclerosis, acute disseminated encephalomyelitis, adrenoleukodystrophy, adrenomyeloneuropathy, Leber's Hereditary Optic Atrophy and related mitochondrial disorders, HTLV-associated Myelopathy and diseases linked to demyelination of PNS nerves.

In other embodiment, there is a method of treating or limiting development of a demyelinating disease in a subject, preferably a human, comprising administering to a subject, preferably a human, a therapeutic amount of a compound of formula (I).

In certain embodiments of the invention, the methods and compounds of the invention reduce the progression of MS in particular.

As used herein, "treating" MS means providing any clinical benefit to a subject with MS. The clinical benefit may be temporary or long-lasting. In various non-limiting embodiments, the treatment results in one or more clinical outcome selected from the group consisting of:

(a) decrease in MS disease progression;
(b) decrease in MS disease severity;
(c) decrease in nerve cell demyelination;
(d) decrease in frequency or severity of relapsing MS attacks;
(e) decrease in MS clinical symptoms;
(f) healing of damaged nerve tissue (neuro-restoration);
(g) increase in remyelination of demyelinated nerves in the central nervous system (neuro-restoration);
(h) protection of damaged nerve tissue from further disease activity (neuroprotection);
(i) promoting neuronal outgrowth (neuro-regeneration) in the central nervous system; and
(j) decrease in disability caused by MS.

As used herein, "limiting development" of MS means providing a limitation in development of symptoms or disease in a subject that is at risk of developing MS. Exemplary subjects at risk of MS include, but are not limited to subjects with a relative (identical twin, non-identical twin, sibling, parent, etc.) that has MS and subjects that, have suffered a clinically isolated syndrome (CIS), which is a subject's first neurological episode, caused by inflammation or demyelinisation of nerve tissue.

The compound of formula (I) according to the invention can be used to treat or limit development of neuromuscular diseases in a mammal, preferably a human.

Preferably, the neuromuscular diseases comprise MN diseases, ALS, PBP, PMA, PLS, SMA, Kennedy's disease, PPS, PPMA, MMN, MMA, paraneoplastic motor neuron disease, LEMS, MG and botulism.

The compounds of formula (I) according to the invention are used to treat or limit development of MN diseases like ALS (amyotrophic lateral sclerosis), PBP (progressive bulbar palsy), PMA (progressive muscular atrophy), PLS (primary lateral sclerosis), SMA (spinal muscular atrophy), Kennedy's disease, PPS (Post-polio syndrome), PPMA (Post-Polio Muscular Atrophy), MMN (Multifocal motor neuropathy), MMA (Monomelic amyotrophy), paraneoplastic motor neuron disease, LEMS (Lambert-Eaton Myasthenic Syndrome), MG (Myasthenia gravis) and botulism, in particular by limiting degeneration of motor neurons.

In certain embodiments of the invention, the methods and compound of formula (I) treat, limit development or reduce the progression of ALS in particular.

As used herein, "treating" ALS means providing any clinical benefit to a subject with ALS. The clinical benefit may be temporary or long-lasting. In various non-limiting embodiments, the treatment results in one or more clinical outcome selected from the group consisting of:

(a) decrease in ALS disease progression;
(b) decrease in ALS disease severity;
(c) decrease in ALS clinical symptoms;

As used herein, "reducing the progression" or "limiting development" of ALS means providing a limitation in development of symptoms or disease in a subject that is at risk of developing ALS.

In some embodiments, there is a method of treating or limiting development of a neuromuscular disease in a subject, comprising the step of administering to the subject a therapeutic amount of the compound of formula (I).

The neuromuscular diseases comprise MN diseases, ALS, PBP, PMA, PLS, SMA, Kennedy's disease, PPS, PPMA, MMN, MMA, paraneoplastic motor neuron disease, LEMS, MG and botulism.

The compounds of formula (I) according to the invention can be used to treat or prevent α-synucleinopathies in a mammal, preferably a human.

Preferably, the compounds of formula (I) are used to treat or prevent Parkinson disease, dementia lewis bodies, multiple system atrophy, Lewis bodies dysphagia, neuroaxonal dystrophies and neurodegeneration with brain iron accumulation type I.

Motor impairments, or impairments of motor function, that can be treated in accordance with the methods described herein include, without limitation: general mobility impairments, walking impairments, gait impairments (e.g., gait freezing), unwanted acceleration of walking, postural instability, stooped posture, increase in falls, dystonia, dyskinesia, tremor, rigidity, bradykinesia, micrographia, dexterity impairment, motor coordination impairment, decreased arm swing, akathisia, speech impairment, problematic swallowing, sexual dysfunction, cramping and drooling. In some embodiments, the motor impairment treated in accordance with the methods described herein is either dyskinesia, dystonia, or motor fluctuation. In other embodiments, the motor impairment is either a tremor, bradykinesia, or rigidity. In certain embodiments, the motor impairment treated in accordance with the methods described herein is an impairment in general mobility. In some embodiments, the motor impairment or the general mobility impairment treated in accordance with the methods described herein is an impairment in walking. In one embodiment, the walking impairment treated in accordance with the methods described herein is a decrease in walking speed. In yet another embodiment, the walking impairment treated in accordance with the methods described herein is unwanted acceleration in walking. In some embodiments, the motor impairment treated in accordance with the methods described herein is increase in falls. In certain embodiments, the motor impairment treated in accordance with the methods described herein is a balance impairment, such as postural instability or postural imbalance.

In some embodiments, the invention provides for a method of preventing, treating or delaying the progression of an α-synucleinopathy in a subject, preferably a human, comprising administering to a subject a therapeutic amount of the compound of formula (I). Preferably, this method is useful wherein said disease is Parkinson disease, dementia with Lewy bodies, multiple system atrophy, Lewy bodies dysphagia, neurodegeneration with brain iron accumulation type I and pure autonomic failure. More preferably, the invention provides for a method of treatment of patients who have Parkinson's disease (PD). In particular, the invention provides for treatment of one or more impairments associated with PD in a patient with PD. In some embodiments, the method prevents, treats or delays the progression of dementia associated with PD in a subject in need of such treatment, comprising administering to said subject a therapeutic effective amount of a compound of formula (I).

The compound of formula (I) according to the invention is formulated for oral or parenteral administration.

A person skilled in the art of pharmaceutical formulation will implement the various useful forms for administration of the formulations of the invention. The formulations containing the compound of formula (I) of the invention may be in liquid, gel, emulsion, solid or injectable form.

These formulations used may additionally include suspensions, emulsions, syrups containing conventionally used inert diluents, and possibly other substances such as wetting agents, sweeteners, preservatives, thickeners, colourings or any other substance known to a person skilled in the art suitable for oral administration, in particular ((sodium sorbate (E201) (Sigma-Aldrich), anthocyanin (E163) (FBC Industries, USA), sodium metabisulphite (E223) (Sigma-Aldrich), alpha-tocopherol (E307) (FBC Industries, USA).

The formulations used may also comprise solvents or other excipients such as water, propylene glycol, vegetable oils or other suitable organic solvents.

The term "excipient" is used to mean any compound which does not interfere with the effectiveness of the biological activity of the formulation according to the invention, and which is not toxic to the host to which it is administered.

The formulation used may also contain adjuvants, such as wetting agents, isotoning agents, emulsifiers, salts or any other substances known to a person skilled in the art that can be used as adjuvants (Polydimethylsiloxane, polyvinyl alcohol (PVA), hydrogels (Carbopol), polyvinylpyrrolidone, hydroxypropyl cellulose (HPC), poloxamer 188, EDTA, chlorobutanol) (Lubrizol, France, Dow Corning, USA).

Advantageously, the formulation may comprise other substances such as vitamins, mineral salts, a pharmaceutically acceptable vector, stabilisers, antioxidants, or any other substance known to a person skilled in the art and intended to be integrated into a drug.

Preferably, the formulation is liquid, orally administrable and contains at least a compound of formula (I), some preservatives, vitamins, water and salt. More preferably, the preservatives are potassium sorbate or benzoate. The vitamin is riboflavin (vitamin B2).

The therapeutic formulation containing the compound of formula (I) of the invention and used in the method of the invention is administered in a pharmaceutically acceptable vehicle.

The terms "pharmaceutically acceptable vehicle" is used to mean any vehicle which does not interfere with the effectiveness of the biological activity of the formulation according to the invention and which is not toxic to the host to which it is administered.

The formulation obtained is usable as a medicinal product for a mammal, and more particularly for humans, to assist in the treatment, prevention or limitation of development of neurodegenerative disorders.

The term "medicinal product" is used to mean a product containing an accurate dose of said preparation according to European directive 65/65/EC, namely any substance or composition described as possessing curative or preventive properties with respect of human or animal disease. For example, the medicinal product containing said preparation at therapeutic doses can be administered orally as a capsule or a tablet, or injected via any other route to confer the beneficial effects.

An appropriate dosage of the therapeutic formulation can be determined by one of skill in the art, taking into consideration the findings described herein together with typical factors such as the body mass of the patient, the physical condition of the patient, and so on. The dosage should contain the therapeutic formulation in an amount that is effective for treating, preventing or limiting development of neurodegenerative disorders, including demyelinating diseases and in particular MS, α-synucleinopathies, including PD, amyloid-related diseases, including AD and MNDs and in particular ALS.

The drug can be administered daily, weekly, or on an intermittent basis. For example, the drug can be administered for three weeks on, followed by one week off, or for two weeks on, followed by one week off, or under other dosing schedules as can be determined by one skilled in the field.

The particular dose selected will depend upon the mode of administration and dosing regimen selected. One preferred schedule is a once daily oral dosing schedule. When longer periods of time are prescribed between each application (typically the case for i.v. administration), each unit dose may be larger than when daily dosages are provided.

The daily dose of the compounds of the invention used may vary according to the needs and severity of symptoms of the patient and according to the route. Typically, the daily dose is between 10 mg/mL and 300 mg/mL of the compound.

Preferably, the daily dose for an adult human is between 30 and 100 mg/mL of the compound of formula (I).

The present invention will be explained in further detail by way of non-limiting examples below, which make reference to the appended drawings. The following methods were used in the experiments described in the examples that follow the description of the methods.

EXAMPLE 1: SYNTHESIS OF THE COMPOUND CR777

In a 150 mL three-neck round-bottom flask, 97 mg (3.1×10-4 mol) of glutathione (L-Glutathione reduced, Aldrich Reagents, France) are solubilized in 10 mL of water, then a solution of withaferin (100 mg, $2.1\times10^{-4}$ mol) (Withaferin A, (4β, 5β, 6β, 22R)-4,27-Dihydroxy-5,6:22,26-diepoxyergosta-2,24-diene-1,26-dione), Aldrich Reagents, France) in 15 mL of THF (Carlo Erba Reagents, France) is slowly added. Under inert atmosphere, the reaction mixture is heated at 65° C. for 8 hours and then stirred for 7 hours at room temperature. The reaction mixture is concentrated under vacuum until THF is removed, then the residual aqueous phase is added with 15 g of Amberlite XAD 16 resin and this heterogeneous mixture is left under strong stirring for 1 hour. The mixture is separated by filtration and the resin is rinsed with 100 mL of water and then desorbed with methanol (Carlo Erba, France) (2×50 mL). The aqueous phase contains excess glutathione. The organic phase is concentrated under reduced pressure to yield a colorless oil which will be purified by High Pressure Liquid Chromatography (HPLC). 45 mg of a white solid are obtained, i.e. a yield of 18%

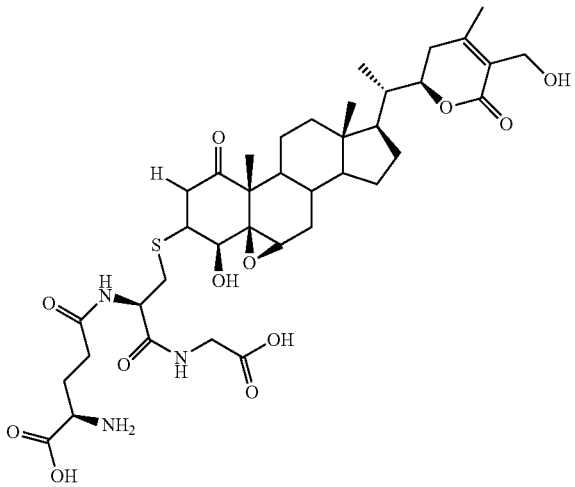

Compound CR777B

In a 100 mL two-neck round-bottom flask, 199 mg ($6.5\times10^{-4}$ mol) of glutathione hydrochloride are solubilized in 8 ml of water and then a solution of CR777B (33.7 mg, $4.3\times10^{-5}$ mol) in THF (12 mL) is slowly added. Under inert atmosphere, the reaction mixture is brought to 65° C. overnight. The reaction mixture is concentrated under vacuum until removal of THF, then the residual aqueous phase is added with 5 g of Amberlite XAD 16 resin and this heterogeneous mixture is left under strong stirring for 1 hour. The mixture is separated by filtration, the resin is rinsed with 100 mL of water and then desorbed with methanol (2×50 mL). The aqueous phase contains excess glutathione. The organic phase is concentrated under reduced pressure to yield a colorless oil which will be purified by High Pressure Liquid Chromatography (HPLC). 7 mg of a white solid are obtained, i.e. a yield of 21% (compound CR777).

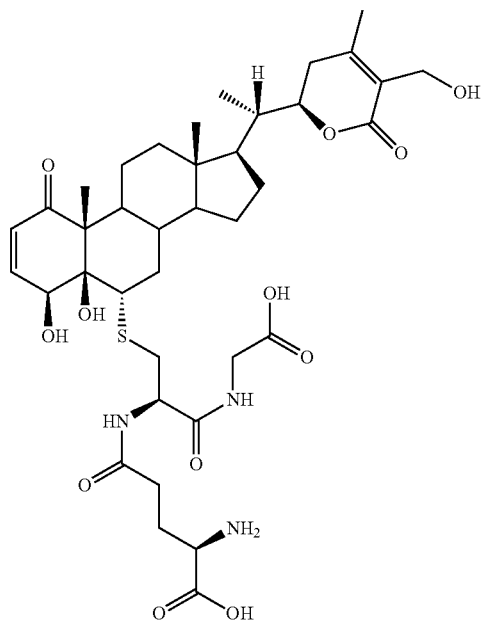

CR777

The sample was analyzed on an analytical HPLC device equipped with a 3.5 μm Sunfire III C18 (4.6×150 mm) reverse phase column (Waters), an Alliance® Waters W2695 HPLC chain equipped with a Waters 2996 PDA detector. This chromatographic system is coupled to a Waters 2424 evaporative light scattering detector (DEDL). The HPLC system is controlled by Empower 3 software (Waters).

The solvents used are composed of ultrapure water (Merck Millipore Q-Gard 1 purification cartridge)+0.1% Formic acid (VWR), acetonitrile (Carlo Erba SDS, HPLC grade, France)+0.1% Formic acid. The standard gradient used is from 0 to 100% acetonitrile in 40 min+10 min to 100% acetonitrile (total duration 50 min). The flow rate is 0.7 mL/min and the injection volume is 20 to 100 μL depending on the sample.

For mass spectrometry, HPLC-MS analyzes are performed on an Alliance® Waters HPLC chain coupled to a Waters 2998 PDA-type UV detector, a DEDL Waters 2420 light scattering detector and a Micromass® ZQ mass detector (Waters).

The solvents are ultrapure HPLC water (Merck Millipore Q-Gard 1 purification cartridge)+0.1% Formic Acid and acetonitrile (Carlo Erba SDS, HPLC grade)+0.1% Formic Acid. The standard gradient used is from 0 to 100% acetonitrile in 40 min+10 min to 100% acetonitrile (total duration 50 min). The flow rate is 0.7 mL/min and the injection volume is 20 to 100 μL depending on the sample. The samples used for HPLC analysis are filtered through 0.45 microns (Ait-France, ref: SFNY 013045N). The compounds are isolated by semi-preparative HPLC on an Alliance® Waters HPLC chain (previously mentioned parameters) equipped with a Sunfire III C18 (10×250 mm) 5 μm reverse phase column (Waters). The standard gradient used is 20 to 45% acetonitrile in 40 min. The flow rate is 4 mL/min and the injection volume is about 200 μL.

The nuclear magnetic resonance experiments were carried out on 300, 500 and 600 MHz Bruker Avance devices using as the solvent deuterated methanol $CD_3OH$ (EurisoTop, France). Chemical shifts are expressed in ppm (parts per million) and calibrated against the reference solvent. The coupling constants are expressed in Hertz (Hz). The multiplicity of signals is expressed by the following abbreviations: s (singlet), ls (wide singlet), d (doublet), dd (doublet of doublets), t (triplet), m (multiplet), q (quadruplet). The signaling of protons and carbons was carried out from 1D $^1H$ and $^{13}C$ one-dimensional experiments, and two-dimensional 2D $^1H$-$^1H$ COSY, $^1H$-$^{13}C$ HSQC or HMQC, $^1H$-$^{13}C$ HMBC, $^1H$-$^1H$ ROESY. NMR spectra are processed using TopSpin (Brucker) dedicated software.

The high resolution mass spectra were performed on a mass spectrometer equipped with an electrospray and a TOF time-of-flight type mass analyzer (LCT®, Waters).

Optical rotations of the compound were measured using a Jasco™ P1010 polarimeter equipped with Spectro Manager software. The monochromatic light source is the sodium D line. The experiments were carried out with a 100 mm quartz tank of 350 μL, and the products were solubilized in methanol.

The infrared (IR) adsorption spectra of the described compound were measured on the Perkin-Elmer Spectrum 100 FT-IR spectrometer. The device is equipped with Spectrum software (version 6.3.5) from Perkin-Elmer. The compounds were prepared in solution in methanol and then dried with compressed air. The absorption bands are given in cm-1.

Elemental analysis is carried out on a Vario ELIII apparatus, with a detection of catharometry type for Carbon, Hydrogen, Nitrogen and Oxygen elements. For the determination of Sulfur, detection is carried out using infra-red.

| | NMR $^1H$ and $^{13}C$ (500 MHz, Methanol –$d_4$) | | | | | |
|---|---|---|---|---|---|---|
| | m/z 591 | | | m/z 777 naturel | | |
| Position | $\delta_C$ | $\delta_H$ (mult; J in Hz) | HMBC | $\delta_C$ | $\delta_H$ (mult; J in Hz) | HMBC |
| 1 | 204.1 | — | | 204.2 | — | |
| 2 | 127.5 | 5.89 (1H; dd; 10.2; 2.0) | C-4, C-10 | 127.5 | 5.89 (1H; dd; 10.2; 2.0) | C-4, C-10 |
| 3 | 148.8 | 6.58 (1H; dd; 10.2, 1.9) | C-1, C-5 | 148.6 | 6.57 (1H; dd; 10.2, 1.9) | C-1, C-5 |
| 4 | 67.3 | 4.89 (1H; m) | C-1, C-2, C-3, C-6 | 67.3 | 4.90 (1H; m) | C-1, C-2, C-3, C-6 |
| 5 | 81.4 | — | | 81.3 | — | |
| 6 | 52.4 | 3.02 (1H; d; 12.3) | C-4, C-5, C-7, C-10, Cys (35.3) | 52.7 | 3.16 (1H; d; 12.3) | C-4, C-5, C-7, Cys (36.3) |
| 7 | 38.7 | 2.19 (1H; m), 1.55 (1H; m) | C-6, C-8, C-9, C-14 | 38.5 | 2.15 (1H; m), 1.51 (1H; m) | C-6, C-8, C-9, C-14 |
| 8 | 36.7 | 1.67 (1H; m) | | 36.6 | 1.66 (1H; m) | |
| 9 | 47.0 | 1.39 (1H; m) | | 47.0 | 1.39 (1H; m) | |
| 10 | 59.3 | — | | 59.2 | — | |
| 11 | 28.4 | 1.81 (1H; m), 1.42 (1H; m) | | 28.5 | 1.81 (1H; m), 1.40 (1H; m) | |
| 12 | 40.5 | 1.14 (1H; m) | | 40.3 | 1.95 (1H; m) | |
| 13 | 44.4 | — | | 44.3 | — | |
| 14 | 56.3 | 1.18 (1H; m) | C-15 | 56.3 | 1.18 (1H; m) | C-15 |

| | NMR $^1$H and $^{13}$C (500 MHz, Methanol $-d_4$) | | | | | | |
|---|---|---|---|---|---|---|---|
| | m/z 591 | | | m/z 777 naturel | | | |
| Position | $\delta_C$ | $\delta_H$ (mult; J in Hz) | HMBC | $\delta_C$ | $\delta_H$ (mult; J in Hz) | HMBC | |
| 15 | 25.2 | 1.70 (1H; m), 1.27 (1H; m) | C-14 | 25.2 | 1.70 (1H; m), 1.29 (1H; m) | C-14 | |
| 16 | 24.3 | 1.39 (1H; m), 0.90 (1H; m) | C-13 | 24.2 | 1.38 (1H; m), 0.89 (1H; m) | C-13 | |
| 17 | 53.1 | 1.23 (1H; m) | | 53.1 | 1.23 (1H; m) | | |
| 18 | 12.4 | 0.75 (3H; s) | C-12, C-13, C14, C-17 | 12.3 | 0.75 (3H; s) | C-12, C-13, C14, C-17 | |
| 19 | 10.5 | 1.25 (3H; s) | C-1, C-5, C-9, C-10 | 10.3 | 1.25 (3H; s) | C-1, C-5, C-9, C-10 | |
| 20 | 40.3 | 1.94 (1H; m) | | 40.3 | 1.94 (1H; m) | | |
| 21 | 13.6 | 0.99 (1H; d; 6.8) | C-17, C-20, C-22 | 13.6 | 0.99 (1H; d; 6.8) | C-17, C-20, C-22 | |
| 22 | 80.1 | 4.44 (1H; d; 13.4) | C-20, C-24 | 80.1 | 4.44 (1H; d; 13.4) | | |
| 23 | 30.8 | 2.52 (1H; d; 17.3), 2.16 (1H; m) | C-22, C-24, C-25 | 30.8 | 2.52 (1H; d; 17.3), 2.14 (1H; m) | C-22, C-24, C-25 | |
| 24 | 157.8 | — | | 157.8 | — | | |
| 25 | 126.4 | — | | 126.4 | — | | |
| 26 | 168.5 | — | | 168.5 | — | | |
| 27 | 56.5 | 4.34 (2H; m) | C-24, C-25, C-26 | 56.5 | 4.34 (2H; m) | C-24, C-25, C-26 | |
| 28 | 20.3 | 2.09 (3H; s) | C-23, C-24, C-25 | 20.2 | 2.09 (3H; s) | C-23, C-24, C-25 | |
| L-Cys | 35.3 | 3.13 (1H; dd; 14.3, 4.7), 2.95 (1H; dd; 14.3, 6.6) | C-6, Cys (55.7) | 36.3 | 3.08 (1H; dd; 13.7, 5.7), 2.81 (1H; dd; 13.7, 7.6) | C-6, Cys (55.0), Cys (172.9) | |
| | 55.7 | 3.70 (1H; m) | Cys (35.3), Cys (172.8) | 55.0 | 4.59 (1H; t; 6.) | Cys (36.3), Cys (172.9), Glu (175.2) | |
| | 172.8 | — | | 172.9 | — | | |
| L-Glu | | | | 27.9 | 2.13 (2H; m) | Glu (55.5), Glu (175.2) | |
| | | | | 33.2 | 2.54 (2H; m) | Glu (55.5), Glu (175.2) | |
| | | | | 55.5 | 3.67 (1H; m) | Glu (27.9), Glu (33.2), Glu (173.9) | |
| | | | | 173.9 | — | | |
| | | | | 175.2 | — | | |
| L-Gly | | | | 42.9 | 3.87 (2H, m) | Cys (172.9), Gly (173.9) | |
| | | | | 172.9 | — | | |
| | | | | 173.9 | — | | |

$[\alpha]^{25}$ + 110° (0.5 g/100 mL MeOH),
High-resolution positive ion (HRMS): Calcd for $C_{38}H_{56}N_3O_{12}S$: 778.3517. Found: 778.3517 $[M + H]^+$
High-resolution negative ion (HRMS): Calcd for $C_{38}H_{54}N_3O_{12}S$: 776.3518. Found: 778.3518 $[M - H]^-$
IR: 3300, 2933, 1653 cm$^{-1}$,

EXAMPLE 2: CYTOTOXICITY TESTS ON THE PRODUCT OF EXAMPLE 1 ACCORDING TO THE INVENTION

Human MRC-5 cell line derived from normal lung tissue and human HCT-116 colorectal carcinoma were obtained from the American Type Culture Collection (ATCC, Rockville, Md.). Primary Human Umbilical Vein Endothelial Cells (HUVEC) isolated from the vein of the umbilical cord were obtained from Promocell (Germany). Cell lines were cultured according to the supplier's instructions. Human HCT-116 cells were grown in Gibco McCoy's 5A supplemented with 10% fetal calf serum (FCS) and 1% glutamine. Human MRC-5 cells were grown in DMEM supplemented with 10% fetal calf serum (FCS) and 1% glutamine. HUVECs were grown in Endothelial Cell Growth Medium 2 which is low-serum (2% V/V) media optimized for the cultivation of endothelial cells from large blood vessels.

Cells were counted using a Vi-cell XR (Beckman Coulter) and their viability assessed by 0.25% trypan blue dye exclusion. They were tested for the presence of mycoplasma before experiments with the Mycoplasma PCR Detection Kit (Applied Biological Materials Inc., Canada) in accordance with the manufacturer instructions and only mycoplasma-free cells were used for further investigations.

Cell lines were maintained at 37° C. in a humidified atmosphere containing 5% $CO_2$. Cell growth inhibition was determined by an MTS assay according to the manufacturer's instructions (Promega, Madison, Wis., USA). For $IC_{50}$ determination, the cells were seeded in 96-well plates ($3 \times 10^3$ cells/well) containing 100/IL of growth medium. After 24 h of culture, the cells were treated with the compound CR777 of example 1 at 8 different final concentrations. Each concentration was obtained from serial dilutions in culture medium starting from the stock solution. Control cells were treated with the vehicle. Experiments were performed in triplicate.

After 72 h of incubation, 20 µL of CellTiter 96® $AQ_{ueous}$ One Solution Reagent was added for 2 h before recording absorbance at 490 nm with a spectrophotometric plate reader. The dose-response curves were plotted with Graph Prism software and the $IC_{50}$ values were calculated using the Graph Prism software from polynomial curves (four or five-parameter logistic equations).

The results show that, whatever the cell line tested, the compound CR777 of example 1 does not show any toxicity at the concentrations tested (see FIGS. 1 *a* to *c*).

EXAMPLE 3: IN VITRO MS MODEL

A reproducible in vitro myelination model based on primary cocultures of central neurons and oligodendrocytes culturing in 96-well plate is used and adapted to high throughput screening.

a) Culture of Neurons/Oligodendrocytes

Neurons/oligodendrocytes were cultured as previously described by Charles et al., 2000. PNAS 97 7585-7590.

Briefly, pregnant Wistar female rats of 17 days gestation were killed by cervical dislocation (Janvier Labs, France) and the foetuses removed from the uterus. The forebrains were removed and placed in ice-cold medium of Leibovitz (L15; Pan Biotech, Germany) containing 2% of Penicillin-Streptomycin (Batch 1451013, PanBiotech) and 1% of bovine serum albumin (BSA) (Batch K180713, Pan Biotech). Cortexes were dissociated by trypsinisation for 20 min at 37° C., with Trypsin EDTA 1× (Batch 7310713, PanBiotech). The reaction was stopped by the addition of Dulbecco's modified Eagle's medium (DMEM) (Batch 9710913, PanBiotech) containing DNAase I grade II at 0.1 mg/mL (Batch H131108, PanBiotech) and 10% of foetal calf serum (Batch 41Q7218K, Invitrogen, France). Cells were then mechanically dissociated by 3 passages through a 10 mL pipette. Cells were centrifuged at 180×g for 10 min at 4° C. temperature on a layer of BSA (3.5%) in L15 medium. The supernatant was discarded and cells of the pellet were re-suspended in DMEM containing 10% of FCS. Cells were then centrifuged at 515×g for 10 min at 4° C. The supernatant was discarded and cells of pellet were re-suspended in a culture medium consisting of Neurobasal (Batch 1625353, Invitrogen) supplemented with 2% of B27 (Batch 1618508, Invitrogen), 2 mM of L-glutamine (Batch 6620314, PanBiotech), 2% of PS solution, 1% of foetal calf serum (FCS) and 10 ng/mL of platelet-derived growth factor (PDGF-AA) (Batch H131205, PanBiotech). Viable cells were counted in a Neubauer cytometer using the trypan blue exclusion test. The cells were seeded at a density of 20000 cells/well in 96 well-plates precoated with poly-L-lysine (Batch 3102256, Beckton-Dickinson, France) and laminin (Batch 083M4034V, Sigma-Aldrich France).

The following day of seeding, cells were incubated with or without the compound CR777 of Example 1 (1, 10, 100 pmol/L, 1, 10, 100 nmol/L, 1 and 10 µmol/L diluted in culture medium). The plates were maintained at 37° C. in a humidified incubator, in an atmosphere of air (95%)-CO2 (5%). Half of the medium was changed every 2 days with fresh medium in presence or absence of compound.

The following conditions were assessed:

Plate 1 for Day 12 (A2B5) and plate 2 for Day 18 (MAG evaluation)
Control (vehicle)
Compound CR777 of example 1 (1 pmol/L)
Compound CR777 of example 1 (10 pmol/L)
Compound CR777 of example 1 (100 pmol/L)
Compound CR777 of example 1 (1 nmol/L)
Compound CR777 of example 1 (10 nmol/L)
Compound CR777 of example 1 (100 nmol/L)
Compound CR777 of example 1 (1 µmol/L)
Compound CR777 of example 1 (10 µmol/L)

b) Immunostaining of Cells

On days 12 and 18 of culture, cells were fixed by a cold mixture of absolute ethanol 95% (Batch SZBD1470V, Sigma) and acetic acid 5% (Batch SZBD1760V, Sigma) for 5 min. The cells were then permeabilized and non-specific sites were blocked with a solution of phosphate buffered saline (Batch 3010914, PanBiotech) containing 0.1% of saponin (Batch BCBJ8417V, Sigma) and 1% FCS for 15 min at room temperature.

On day 12, cells were incubated with Monoclonal Anti-A2B5 conjugated Alexa Fluor® 488 produced in mouse (Batch 2281669, Millipore, France) at dilution of 1/200 in PBS containing 1% FCS, 0.1% saponin, and with anti-MAP-2 antibody produced in chicken (Batch GR180541-3, AbCam; United Kingdom) at dilution of 1/1000 in PBS containing 1% FCS, 0.1% saponin for 2 h at room temperature. This antibody was revealed with Alexa Fluor 568 goat anti-chicken antibody (Batch 1383072, Molecular probe; France) at the dilution of 1/400 in PBS with 1% FCS, 0.1% saponin, for 1 h at room temperature.

On day 18, cells were incubated with Monoclonal Anti-MAG antibody produced in mouse (Batch 2301638, Millipore) at dilution of 1/400 in PBS containing 1% FCS, 0.1% saponin, and with anti-MAP-2 antibody produced in chicken at dilution of 1/1000 in PBS containing 1% FCS, 0.1% saponin for 2 h at room temperature. These antibodies were revealed with Alexa Fluor 488 goat anti-mouse antibody (Batch 1397999, Molecular probe) at the dilution of 1/400 in PBS with 1% FCS, 0.1% saponin and Alexa Fluor 568 goat anti-chicken antibody at the dilution of 1/400 in PBS with 1% FCS, 0.1% saponin, for 1 h at room temperature.

c) Results

The immunolabeled cultures were automatically examined with ImageXpress (Molecular Devices) equipped with a LED at ×20 magnification. For each condition, 30 pictures (representing ~80% of the total surface of the well) per well were taken. All images were taken with the same conditions. Number of A2B5 positive cells and number of MAG positive cells were automatically analyzed by using Custom module editor (Molecular Devices). Data were expressed in percentage of control conditions (no plant extract=100%). All values were expressed as mean+/−SEM (s.e.mean) of the 6 wells. Graphs and statistical analyses are made on the different conditions (ANOVA followed by Dunnett's test when allowed, using GraphPad Prism software).

Treatment with compound CR777 did not show any significant increase of the OPC (precursor cells of oligodendrocytes) number after 12 days treatment (FIG. 2). At the highest doses, decrease of the total number of OPCs was observed (by an inhibition of the proliferation of the cells or by a toxic effect).

Compound CR777 after 18 days of treatment was able to increase the number of MAG positive cells and significantly improved the myelination of neurons by OL. This effect was significant at all doses (from 1 pmol/L up to 1 μmol/L) except for the highest concentration (10 μM). Interestingly, the compound CR777 displayed a maximal effect for all doses (~60% of increase) (FIGS. 3 a and b). Myelin Associated Glycoprotein (MAG) is a specific protein of differentiated oligodendrocytes that is heavily expressed in myelinating oligodendrocytes (Bradl. M., & H. Lassmann., 2010. Acta Neuropathol (2010) 119:37-53).

EXAMPLE 4: NEUROPROTECTIVE EFFECT FOLLOWING EXPOSURE TO MPP+

This study investigated the neuroprotective effect of the Compound CR777 of example 1 on rat primary mesencephalic cultures following exposure to 1-methyl-4-phenyl pyridinium ($MPP^+$).

The neurotoxic 1-methyl-4-phenyl-1,2,3,6-tetrahydropyridine (MPTP) is a specific dopaminergic neuronal toxin. MPTP is converted to $MPP^+$ by astroglia and then causes specific dopaminergic neuronal death in the SN, thus leading to the clinical symptoms of PD in humans, primates and mice (Visanji et al., 2008 FASEB J. 2008; 22(7):2488-97, Giordano S, et al., PLoS One. 2012; 7(9)). $MPP^+$ selectively enters dopamine neurons via the dopamine transporter and also blocks complex I of the mitochondrial respiratory chain.

In such assay, Brain Derived Growth Factor (BDNF) was used as standard molecule.

a) Culture of Mesencephalic Dopaminergic Neurons

Rat dopaminergic neurons were cultured as described by Visanji et al., 2008 FASEB J. 2008; 22(7):2488-97. Briefly, the midbrains obtained from 15-day old rat embryos (Janvier Labs, France) were dissected under a microscope. The embryonic midbrains were removed and placed in ice-cold medium of Leibovitz (L15, Batch 4290114, Pan Biotech, Germany) containing 2% of Penicillin-Streptomycin (PS, Batch 1451013, Pan Biotech) and 1% of bovine serum albumin (BSA, Batch K030913, Pan Biotech). The ventral portion of the mesencephalic flexure, a region of the developing brain rich in dopaminergic neurons, was used for the cell preparations.

The midbrains were dissociated by trypsinisation for 20 min at 37° C. (Trypsin 0.05%, EDTA 0.02% (Batch 7310713, PanBiotech). The reaction was stopped by the addition of Dulbecco's modified Eagle's medium (DMEM, Batch 9710913, PanBiotech) containing DNAase I grade II (0.1 mg/mL, Batch H131108, PanBiotech) and 10% of foetal calf serum (FCS, Batch 41Q7218K, Gibco). Cells were then mechanically dissociated by 3 passages through a 10 mL pipette. Cells were then centrifuged at 180×g for 10 min at +4° C. on a layer of BSA (3.5%) in L15 medium. The supernatant was discarded and the cell pellets were resuspended in a defined culture medium consisting of Neurobasal (Batch 1576979, Invitrogen, France) supplemented with 2% of B27 (Batch 1589889, Invitrogen), 2 mM of L-glutamine (Batch 8150713, PanBiotech), 2% of PS solution, 10 ng/mL of Brain-derived neurotrophic factor (Batch H140108, PanBiotech,) and 1 ng/mL of Glial-Derived Neurotrophic Factor (Batch H130917, Pan Biotech) Viable cells were counted in a Neubauer cytometer using the trypan blue exclusion test. The cells were seeded in supplemented neurobasal medium at a density of 40 000 cells/well in 96 well-plates pre-coated with poly-L-lysine (Batch 3102256, Corning Biocoat) and maintained in a humidified incubator at 37° C. in 5% CO2/95% air atmosphere. Half of the medium was changed every 2 days with fresh medium.

b) MPP+ Exposure

On day 6 of culture, the medium was removed and fresh medium was added, without or with MPP+ at 4 μM diluted in control medium and let for 48 h. In parallel, compound CR777 was solved in culture medium and then pre-incubated with mesencephalic neurons 1 hour before the MPP+ application (48 h).

The following conditions were assessed: (6 wells per condition)
Control (vehicle)
Compound CR777 of example 1 (1 pmol/L)
Compound CR777 of example 1 (10 pmol/L)
Compound CR777 of example 1 (100 pmol/L)
Compound CR777 of example 1 (1 nmol/L)
Compound CR777 of example 1 (10 nmol/L)
Compound CR777 of example 1 (100 nmol/L)
Compound CR777 of example 1 (1 μmol/L)
Compound CR777 of example 1 (10 μmol/L)

c) Immunostaining 48 hours after intoxication, the cell culture supernatant was taken off and the dopaminergic neurons were fixed by a solution of 4% paraformaldehyde in PBS, pH=7.3 for 20 min at room temperature.

After permeabilization with 0.1% of saponin (Merck, France), cells were incubated for 2 hours with monoclonal Anti-Tyrosine Hydroxylase (TH) antibody (ref T1299, Sigma Aldrich, France) produced in mouse at dilution of 1/10000 in PBS containing 1% FCS, 0.1% saponin, for 2 h at room temperature.

This antibody was revealed with Alexa Fluor 488 goat anti-mouse IgG at the dilution 1/800 in PBS containing 1% FCS, 0.1% saponin, for 1 h at room temperature.

d) Results

The immunolabeled cultures were automatically examined with ImageXpress (Molecular Devices, United Kingdom) equipped with a LED at ×10 magnification. For each condition (6 culture wells), 20 automatically fields per well (representing ~80% of the total surface of the well) were analyzed. All images were taken with the same conditions. Analysis were automatically performed by using Custom Module Editor (Molecular Devices).

Data were expressed in percentage of control conditions (no injury, no compound=100%). All values were expressed as mean+/−SEM (standard error mean) of the 6 wells with statistical analyses on the different conditions (ANOVA followed by Dunnett's test when allowed, using GraphPad Prism software).

MPP+ induced a significant TH positive neuron cell death (>35%) as already published (Visanji et al., 2008).

The compound CR777 added 1 h before MPP+ and let for 48 h, significantly protected neurons from death. All concentrations displayed protective effect but more particularly between 10 and 100 nmol/L (FIG. 4).

e) Conclusion $MPP^+$ (4 μM-48 h) applied on primary mesencephalic culture induced a significant TH positive neuron (dopaminergic neurons) death.

Compound CR777, tested at concentrations between 10 and 100 nmol/L showed an important and significantly neuro-protective effect on $MPP^+$ induced injuries.

EXAMPLE 5: NEUROPROTECTIVE EFFECT FOLLOWING EXPOSURE TO 6-OHDA

This study investigated the mode of action of CR777 on rat primary mesencephalic cultures following exposure to 6-OHDA. The effect of CR777 on level of GDNF and BDNF mRNA was investigated after 24 h 6-OHDA incubation and CR777. The main pathways of survival, regulation of the apoptosis and neuronal growth were investigated in presence of CR777 and inhibitors of these different pathways. The following pathways were investigated using antagonists of different proteins of interest:

RAS (small GTPase)/RAF (proto-oncogene Serine/threonine kinase);
Peroxisome proliferator-activated receptor gamma (PPAR-γ) (nuclear receptor)
The Pi3K/AKT/mTor (cell signaling pathway that plays a key role in cellular homeostasis through its role in regulation of apoptosis, cell growth, cell cycle).
NO (nitric oxide) pathway a) Culture of Mesencephalic Neurons Rat dopaminergic neurons were cultured as described in Example 4.

b) 6-OHDA Exposure

On day 6 of culture, the medium was removed and fresh medium was added, without or with 6-OHDA (Sigma, Batch: 083M4624V) at 20 µM diluted in control medium and let for 48 h. In parallel, all inhibitors were solved in culture medium and were added 2 h before the 6-OHDA application (namely 1 h before test compounds application).

CR777 was solved in DMSO at 10 mM, diluted in culture medium and then pre-incubated with mesencephalic neurons 1 hour before the 6-OHDA application (48 h). 6 wells per condition were assessed.

For survival and α-syn aggregation, compound was tested on 1 culture in a 96 well-plate (6 wells per condition), was pre-incubated 1 hour before 6-OHDA and let for 48 hours.

The following conditions were assessed:
Control (culture medium)
+6-OHDA (20 µM, 48 h)
+6-OHDA (20 µM, 48 h)+CR777 1 µM
+6-OHDA (20 µM, 48 h)+CR777 100 nM
+6-OHDA (20 µM, 48 h)+CR777 10 nM
+6-OHDA (20 µM, 48 h)+CR777 1 nM For pathway investigation, the compound was tested on one primary dopaminergic culture in 96 well plates (6 wells per conditions).

Inhibitors were pre-incubated for 2 hours before 6-OHDA application and CR777 was pre-incubated 1 hour before 6-OHDA application.

The following conditions were assessed:
Control (culture medium)
+6-OHDA (20 µM)
+6-OHDA (20 µM)+CR777 10 nM+FTS (4 µM)
+6-OHDA (20 µM)+CR777 10 nM+BEZ235 (40 nM)
+6-OHDA (20 µM)+CR777 10 nM+L-NAME (100 µM)
+6-OHDA (20 µM)+CR777 10 nM+T0070907 (1 µM)
+6-OHDA (20 µM)+CR777 10 nM+ABT 199 (5 µM)

The antagonists/inhibitors used in the experiments are the following:
FTS: farnesylthiosalicylic acid selectively disrupts the association of chronically active Ras proteins with the plasma membrane.
BEZ-235: dual PI3K/mTOR inhibitor.
T0070907: selective PPAR-γ antagonist L-NAME (Nitro-L-arginine methyl ester): precursor to NOS inhibitor, L-NNA—requires bioactivation to become a fully functional inhibitor.
ABT-199: selective inhibitor of Bcl-2.

For Western blot analysis, the compound CR777 was tested at the concentration of 10 nM on one primary dopaminergic culture in 24 well plates (4 wells per conditions), and incubated 24 hours c) Immunostaining for Survival and α-Syn Aggregation 48 hours after intoxication, the cell culture supernatant was taken off and the dopaminergic neurons were fixed by a solution of 4% paraformaldehyde in PBS, pH=7.3 for 20 min at room temperature.

After permeabilization with 0.1% of saponin, cells were incubated for 2 hours with:
monoclonal Anti-Tyrosine Hydroxylase (TH) antibody produced in mouse at dilution of 1/10000 in PBS containing 1% FCS, 0.1% saponin,
polyclonal anti-α-syn antibody produced in rabbit at dilution of 1/200 for 2 h at room temperature.

This antibody was revealed with Alexa Fluor 488 goat anti-mouse IgG at the dilution 1/800 in PBS containing 1% FCS, 0.1% saponin and with Alexa fluor 568 goat anti-rabbit IgG at the dilution 1/400 in PBS containing 1% FCS, 0.1% saponin, for 1 h at room temperature.

For each condition, 20 pictures/well (representative of ~the all well area) were automatically taken using ImageXpress (Molecular Devices) with 10× magnification. All images were taken with the same conditions. Analysis were automatically performed by using Custom Module Editor (Molecular Devices).

The following endpoint was investigated for each culture well:
The total dopaminergic neuron survival (TH staining),
The total area of α-syn on TH positive neuron (overlapping α-syn/TH)

The results are exposed on FIGS. 5, 6 and 7.

It can be seen that 6-OHDA (20 µM, 48 h) induced a large and significant TH positive neuronal death (~30%) and loss of the neurite network (~35%). In addition, a large and significant α-syn aggregation inside TH neuron cytoplasm was observed.

CR777 added 1 h before 6-OHDA and let for 48 h, significantly protected neurons from death at 10 nM (the effect followed a bell shape curve).

In particular, CR777 shown a significant protective effect on dopaminergic neurite network at all concentrations tested. Moreover, a significant effect was also observed on α-syn aggregation. CR777 at 10 and 100 nM, was able to reduce the aggregation of the protein.

d) Immunostaining for Inhibitors 48 hours after intoxication, the cell culture supernatant was taken off and the dopaminergic neurons were fixed by a solution of 4% paraformaldehyde in PBS, pH=7.3 for 20 min at room temperature.

After permeabilization with 0.1% of saponin, cells were incubated for 2 hours with monoclonal Anti-Tyrosine Hydroxylase (TH) antibody produced in mouse at dilution of 1/10000 in PBS containing 1% FCS, 0.1% saponin, for 2 h at room temperature.

This antibody was revealed with Alexa Fluor 488 goat anti-mouse IgG at the dilution 1/800 in PBS containing 1% FCS, 0.1% saponin, for 1 h at room temperature.

For each condition, 20 pictures/well (representative of ~the all well area) were automatically taken using ImageXpress (Molecular Devices) with 10× magnification. All images were taken with the same conditions. Analysis were automatically performed by using Custom Module Editor (Molecular Devices).

The total dopaminergic neuron survival (TH staining) was investigated for each culture well.

The measure of TH overexpression in mesencephalic neurons (Western blotting analysis) has been assessed.

Briefly, on day 6 of culture, the medium was removed, and fresh medium was added, without or with test compounds (at 1 concentration), 1 h later 6-OHDA (20 µM) was added. Twenty-four hours after the start of 6-OHDA exposure, the cells were lysed with CelLyticMT reagent.

For each condition, the quantity of protein was determined using the micro kit BCA (Pierce). Briefly, lysates were diluted at 1/20 in PBS and mixed, in equal volume, with a micro BCA Working reagent. These solutions were incubated at 60° C. during 1 hour and the quantity of protein was measured at 562 nm with a spectrophotometer Nanovue (GE Healthcare) and compared with the standard of Bovin Serum Albumin curve (BSA, Pierce).

The solutions were diluted in water for Molecular Biology at 1 mg/ml final concentration of protein (hereinafter "protein samples"). All reagents were prepared and used according to manufacturer's recommendations for use on Simon™ (ProteinSimple, San Jose, Calif., www.proteinsimple.com/simon.html). Reagents included biotinylated molecular weight ladder, streptavidin-HRP, fluorescent standards, luminol-S, hydrogen peroxide, sample buffer, DTT, stacking matrix, separation matrix, running buffer, wash buffer, matrix removal buffer, capillaries, containing a proprietary UV-activated chemical linked reagent, and antibody diluent and antibodies (goat-anti mouse secondary antibody). 6 µl of protein samples (see above) diluted 3:1 by adding 2 µl of the 2× master mix (containing 80 mM DTT, 2× sample buffer and 2× fluorescent standards). Each final protein sample was boiled 5 min at 95° c. and 5 µl applied to proper wells.

The Simon™ Instrument was prepared by adding 2 ml of matrix removal buffer to trough 1, 2 ml of wash buffer to trough 2, and 0.8 ml of running buffer to trough 3. Capillaries and the 384-well plate containing samples, antibodies, and matrices were then placed inside the instrument. The simple Western was run with capillaries filled with separation matrix for 150 s, stacking matrix for 12 s and protein extracts for 8 s. The samples were then separated with 250 V for 40 min and then immobilized to the capillary wall using default immobilization conditions and washed with matrix removal buffer for 140 s to remove the separation matrix. Capillaries were then washed with wash buffer for 150 s and blocked with antibody diluent for 15 min. Next, capillaries were incubated with anti-TH and anti-GAPDH primary antibodies (2 h), washed, and incubated with HRP conjugated secondary antibodies for 1 h. After removal of unbound secondary antibody, the capillaries were incubated with the luminol-S/peroxide substrate and chemiluminescent signal was collected using the Charge-Coupled Device (CCD) camera of Simon™ with six different exposure times (30, 60, 120, 240, 480, and 960 s). Data analysis were performed using the Compass Software (ProteinSimple) on Simon™ e) Results

The results show that 6-OHDA induced a large and significant TH neuronal death (by 30%) and neurite network lose (~40%). CR777 added 1 h before 6-OHDA showed a significant protective effect when tested at the concentration of 10 nM.

This compound was incubated in presence of different inhibitors, and its effect has been evaluated (FIG. 8).

FTS inhibitors: Ras/Raf pathway inhibitors.

Mitogen-activated protein kinases (MAPKs) pathways are activated by diverse extracellular and intracellular stimuli including peptide growth factors, cytokines, hormones, and various cellular stressors such as oxidative stress and endoplasmic reticulum stress.

Inhibition of Ras/Raf pathway did not induce any changes into the neuroprotective effect of CR777.

BEZ235 inhibitor: PI3K/AKT/mTOR pathway inhibitor.

The PI3K/AKT pathway is involved in survival and inhibition of apoptosis in different cell types. Growth factors such as insulin-like growth factor-1 (IGF1) promote survival through PI3K activity and phosphorylation of AKT at serine residue 473 (Ser473), but proliferative cytokines, like interleukin 3 (IL-3), also promote survival via PI3K activity and phosphorylation of AKT in lymphoblasts.

The kinase mTOR is a major negative regulator of autophagy and the PI3K/AKT pathway is an upstream major modulator of mTORC1. In addition, autophagy is the major cellular digestion process that removes damaged macromolecules and organelles. Autophagy is critical to providing energy and molecular building blocks by recycling macromolecules in response to nutrient and environmental stress.

Among several growth factors tested, brain-derived neurotrophic factor (BDNF), the most prominent neurotrophic factor in the CNS, has been shown to activate mTORC1 signaling and enhance novel protein synthesis in cortical neurons. BDNF activates both Akt and MAPK. In addition to BDNF and insulin, several growth factors/RTKs and guidance molecules such as Eph, Slit, and Reelin have been reported to activate mTORC1 signaling in neuronal cells (Takei et al., 2014).

In presence of a PI3K/AKT/mTOR pathway inhibitor, the neuroprotective effect of CR777 is fully abolished.

L-NAME inhibitor: nNOS pathway inhibitor.

The neuronal isoform of nitric oxide (NO) synthase (nNOS) is activated in response to $Ca^t$/calmodulin to produce the diffusible second-messenger NO. NO plays a key role in driving the long-term molecular changes underlying neuroplasticity by linking NMDAR signaling to downstream gene expression programs (Gallo et al., 2011).

Inhibition of nNOS pathway did not induce any changes of the neuroprotective effect of CR777.

T0070907 inhibitor: PPARγ pathway inhibitor.

Peroxisome proliferator activated receptors (PPARs) are nuclear receptors that induce signaling and transcription of different pathways.

PPARγ is a transcriptional factor regulating the expression of multiple genes, it promotes the development and health of neurons. Accumulative evidence suggests that PPARγ induces neuronal differentiation by a mechanism that implicates activation of PPARγ-dependent transcription and also activation of secondary pathways.

In presence of T0070907, PPARγ pathway inhibitor, no effect was observed on the neuroprotective action of the CR777.

ABT-199 inhibitor: Bcl2 pathway inhibitor.

Bcl-2 family regulates cell death in the mature nervous system, pharmacological manipulation of Bcl-2 family action could prove beneficial in the treatment of human neurological conditions such as stroke and neurodegenerative diseases.

Inhibition of Bcl2 pathway did not induce any changes in the neuroprotective effect of CR777.

In light of these results the following conclusions could be drawn on the mode of action CR777:

CR777 was able to protect TH positive neurons from 6-OHDA and partially protected neurons from the α-syn aggregation.

CR777 has a neuroprotective effect involved the Pi3K pathway.

EXAMPLE 6: EFFECT IN RAT PRIMARY CORTICAL NEURONS AFTER GLUTAMATE INJURY a) Culture of Cortical Neurons Rat cortical neurons were cultured as described by Singer C. A., et al., 1999. J Neurosci 19: 2455-2463 and Callizot. N., et al., 2013 J Neurosci Res. 91: 706-16.

Briefly, pregnant Wistar females (Janvier Labs, France) at 15 days of gestation were killed by cervical dislocation. Foetuses were collected and immediately placed in ice-cold L15 Leibovitz medium (Batch: 4290114, Pan Biotech, Germany) with a 2% penicillin (10,000 U/mL) and streptomycin (10 mg/mL) solution (PS Batch: 7500912; Pan Biotech,) and 1% bovine serum albumin (BSA Batch: K030913; Pan Biotech,). Cortex was treated for 20 min at 37° C. with a trypsin-EDTA solution (Batch: 7310713, Pan Biotech,) at a final concentration of 0.05% trypsin and 0.02% EDTA. The dissociation was stopped by addition of Dulbecco's modified Eagle's medium (DMEM) with 4.5 g/L of glucose (Batch: 9710913, Pan Biotech,), containing DNAse I grade II at the final concentration of 0.5 mg/mL (Batch: H131108, Pan Biotech,) and 10% fetal calf serum (Batch: 41Q7218K, Invitrogen, France). Cells were mechanically dissociated by three forced passages through the tip of a 10-mL pipette. Cells were then centrifuged at 515 g for 10 min at 4° C. The supernatant was discarded, and the pellet was resuspended in a defined culture medium consisting of Neurobasal medium (Batch: 1576979, Invitrogen) with a 2% solution of B27 supplement (Batch: 1589889, Invitrogen,), 2 mmol/L of L-glutamine (Batch: 5030513, Pan Biotech,), 2% of PS solution, and 10 ng/mL of brain-derived neurotrophic factor (BDNF) (Batch: H140108, Pan Biotech). Viable cells were counted in a Neubauer cytometer, using the trypan blue exclusion test. Once obtained, the cells were seeded at a density of 30,000 per well in 96-well plates precoated with poly-L-lysine (Batch: 3102256, Corning Biocoat) and were cultured at 37° C. in an air (95%)—$CO_2$ (5%) incubator. The medium was changed every 2 days. The cortical neurons were intoxicated with glutamate solution.

a) Intoxication with the Glutamate

On day 13 after culture, glutamate (Batch: 061M0030V, Sigma) was added into cell culture to a final concentration of 40 µM diluted in control medium for 20 min. After 20 min, the cells were washed-out and new fresh medium containing or not the compound CR777 was added for 48 h additional time.

CR777 (1, 10, 100 pmol/L, 1, 10, 100 nmol/L, 1, 10 µmol/L) were solved and diluted in culture medium and then pre-incubated with primary cortical neurons for 1 hour before the glutamate application.

The following conditions were assessed:
Control (culture medium)
+ glutamate (40 µM, 20 min)
+ glutamate (40 µM, 20 min)+CR777 (at each concentration)

b) Immunostaining: Neuron Survival

After 48 hours of glutamate intoxication, cells were fixed by a cold solution of ethanol at 95% (Batch: SZBD1470V, Sigma) and acetic acid 5% (Batch: SZBD1760V, Sigma) for 5 min at −20° C. After permeabilization with 0.1% of saponin (Batch: BCBJ8417V, Sigma), cells were incubated for 2 h with mouse monoclonal antibody anti microtubule-associated-protein 2 (MAP-2) (Batch: 063M4802; Sigma) at dilution of 1/400 in PBS containing 1% foetal calf serum and 0.1% of saponin.

This antibody was revealed with Alexa Fluor 488 goat anti-mouse IgG at the dilution of 1/400 in PBS containing 1% foetal calf serum and 0.1% of saponin for 1 h at room temperature.

c) Analysis of Neuron Survival and Neurite Network

The immunolabeled cultures were automatically examined with ImageXpress equipped with a LED at ×20 magnification. For each condition (6 culture wells), 30 automatically fields per well (representing ~80% of the total surface of the well) were analyzed. The total number of neurons and neurite length were automatically analyzed using MetaXpress software.

d) Results

The accumulation of glutamate can excessively activate the N-methyl-d-aspartate (NMDA) receptors and cause excitotoxicity. Glutamate (40 µM-20 min) applied on primary cortical neuron culture induced a significant neuronal death and neurite network loss.

CR777 added 1 h before glutamate and let for 48 h, significantly protected neurons from death at low concentrations (100 pM). The effect was dependent of the dose and the maximal effect was reached at 10 nM. A full protection was observed from 1 nM up to 1 µM (FIG. 9a). In addition, moderate neuroprotective effect was observed on the neurite network. Only the doses of 10, 100 pM and 1 µM significantly protected the neurite network. The maximal effect was observed for 1 µM (FIG. 9b).

EXAMPLE 7: NEUROPROTECTIVE EFFECT ON AN IN VITRO MODEL OF ALZHEIMER DISEASE

The brains of Alzheimer's disease patients have large numbers of plaques (extracellular deposits) that contain amyloid beta (Aβ) peptides which are believed to play a pivotal role in AD pathology. These peptides contribute to cerebrovascular lesions and are neurotoxic. This study investigated the neuroprotective effect of the plant extract of the invention on rat primary cortical cultures following exposure to Aβ1-42 in an in vitro AD model (Callizot. N., et al., 2013).

a. Culture of Cortical Neurons

Rat cortical neurons were cultured as described in Example 6.

The cortical neurons were intoxicated with amyloid beta peptides solutions after 11 days of culture in presence of tested compound CR777.

b) Preparation of Solutions

The Amyloid beta peptide 1-42 (Aβ1-42) preparation was done following the procedure described by Callizot. N., et al., 2013 J Neurosci Res. 91: 706-16. Briefly, Aβ1-42 peptide (Batch: APN09080-1-1, Abcam, United Kingdom) was dissolved in the defined culture medium B27 mentioned above, devoid of serum, at an initial concentration of 40 µmol/L. This solution was gently agitated for 3 days at 37° C. in the dark and immediately used after being properly diluted in culture medium to the concentrations used (20 µM corresponding to 2 µM of AβO, measuring by WB, for survival, neurite network, tau phosphor and caspase 3 activation and 2.5 µM corresponding to 0.25 µM of AβO, for synapses evaluation).

CR777 was solved in DMSO at 10 mM and diluted in culture medium at different concentrations (see table below). The compound was tested on one primary cortical culture in 96 well plates (6 wells per conditions), and was pre-incubated 1 hour before Aβ1-42 application for 24 hours.

The following conditions were assessed:

Plate 1 (MAP-2/tau phospho) or Plate 2 (MAP-2/Caspase 3)
Control
+Aβ1-42 (2004, 24 h)+CR777 (1 µM)
+Aβ1-42 (2004, 24 h)+CR777 (100 nM)
+Aβ1-42 (2004, 24 h)+CR777 (10 nM)
+Aβ1-42 (2004, 24 h)+CR 777 (1 nM)

24 hours after intoxication, the cell culture supernatant was taken off and the cortical neurons were fixed by a cold solution of ethanol (95%) and acetic acid (5%) for 5 min at −20° C.

Plate 1: Immunostainning (MAP-2/Tau Phosphor)

After permeabilization with 0.1% of saponin, cells were incubated for 2 hours with a) a mouse monoclonal antibody anti phosphoT at dilution of 1/400 in PBS containing 1% fetal calf serum and 0.1% of saponin and b) a chicken polyclonal antibody anti microtubule-associated-protein 2 (MAP-2) at dilution of 1/1000 in PBS containing 1% fetal calf serum and 0.1% of saponin (this antibody stains specifically cell bodies and neurites, allowing study of neuronal cell survival and neurite network).

These antibodies were revealed with Alexa Fluor 488 goat anti-mouse IgG and Alexa Fluor 568 goat anti-chicken IgG at the dilution 1/400 in PBS containing 1% FCS, 0.1% saponin, for 1 hour at room temperature.

For each condition, 30 pictures/well (representative of ~the all well area) were taken automatically using ImageXpress (Molecular Devices) with 20× magnification. All images were taken with the same conditions. Analysis were performed automatically by using Custom Module Editor (Molecular Devices).

The following endpoints were investigated per culture well:
The total neuron survival (MAP-2 staining),
The neurite network (MAP-2 staining) and
hyperphophorylation of T protein (pT) into neurons (pT/MAP-2).

Plate 2: Immunostainning (MAP-2/Caspase 3)

After permeabilization with 0.1% of saponin, cells were incubated for 2 hours with a) a mouse monoclonal antibody anti microtubule-associated-protein 2 (MAP-2) at dilution of 1/400 in PBS containing 1% foetal calf serum and 0.1% of saponin and b) a Rabbit polyclonal antibody anti-caspase 3 at the dilution of 1/500 in PBS containing 1% foetal calf serum (Invitrogen) and 0.1% of saponin These antibodies were revealed with Alexa Fluor 488 goat anti-mouse IgG and Alexa Fluor 568 goat anti-rabbit IgG at the dilution of 1/400 in PBS containing 1% foetal calf serum and 0.1% of saponin for 1 h at room temperature.

For each condition, 30 pictures/well (representative of ~the all well area) were taken automatically using ImageXpress (Molecular Devices) with 20× magnification. All images were taken with the same conditions. Analysis were performed automatically by using Custom Module Editor (Molecular Devices).

The total number of caspase 3 positive neuron (overlapping caspase3/MAP-2) were investigated per culture well:

c) Results

Data is expressed in percentage of control conditions (no injury, no compound=100%). All values are expressed as mean+/−SEM (standard error of the mean) from 6 wells per condition per culture. Neuro-Sys performed graphs and statistical analyses on the different conditions (ANOVA followed by Dunnett's test when allowed, using GraphPad Prism software version 5.0).

The results show that Aβ induced a large and significant neuronal death (by 30%) and neurite network lose (~40%) as previously described (Callizot et al., 2013). Aβ induced an increase of the hyperphosphorylation of tau and an activation of caspase 3 on the neurons.

CR777 added 1 h before Aβ showed a significant protective effect at all the concentration tested (1 nM to 1 µM) on neuron survival and on neurite network. CR777 induced a significant decrease of tau hyperphosphorylation and a decrease of caspase 3 activation at all doses (FIG. 10 a to d).

EXAMPLE 8: PRIMARY MOTOR NEURON CULTURE SURVIVAL

The aim of this study was to study the effect of CR777 on primary motor neuron culture from rat spinal cord (SC) injured by glutamate exposure (a well validated in vitro ALS model and model of motor neuron diseases).

a) Culture of Spinal Cord (SC) Motor Neurons

Rat SC motor neurons were cultured as described by Martinou et al., Neuron. 1992 April; 8(4):737-44 and Wang et al., Hum Mol Genet. 2013 Dec. 1; 22(23):4706-19. Briefly, pregnant female rats (Wistar, Janvier labs) of 14 days gestation were killed by cervical dislocation. Foetuses were collected and immediately placed in ice-cold L15 Leibovitz medium (Batch: 4001014, Pan Biotech) with a 2% penicillin (10,000 U/mL) and streptomycin (10 mg/mL) solution (PS; Pan Biotech, batch: 3090914) and 1% bovine serum albumin (BSA; Pan Biotech, batch: h140603). SC were treated for 20 min at 37° C. with a trypsin-EDTA (Pan Biotech, batch: 5890314) solution at a final concentration of 0.05% trypsin and 0.02% EDTA. The dissociation was stopped by addition of Dulbecco's modified Eagle's medium (DMEM) with 4.5 g/liter of glucose (Pan Biotech, batch: 6031214), containing DNAse I grade II (final concentration 0.5 mg/mL; Pan Biotech, batch: H140508) and 10% fetal calf serum (FCS; Invitrogen, batch: 41Q7218K). Cells were mechanically dissociated by three forced passages through the tip of a 10-mL pipette. Cells were then centrifuged at 180 g for 10 min at +4° C. on a layer of BSA (3.5%) in L15 medium. The supernatant was discarded, and the pellet was resuspended in Neurobasal medium (Invitrogen, batch: 1704746) with a 2% solution of B27 supplement (Invitrogen, batch: 1668967), 2 mmol/L of L-glutamine (Pan Biotech, batch: 6620314), 2% of PS solution, and 10 ng/mL of brain-derived neurotrophic factor (BDNF; Pan Biotech, batch: H140108). Viable cells were counted in a Neubauer cytometer, using the trypan blue exclusion test. The cells were seeded at a density of 20,000 per well in 96-well plates precoated with poly-L-lysine (Biocoat, batch: 21614030) and were cultured at 37° C. in an air (95%)-CO2 (5%) incubator. The medium was changed every day.

b) CR777 and Glutamate Exposure

On day 13, glutamate was added into cell culture to a final concentration of 5 μM diluted in control medium in presence or absence of the compound CR777 of example 1 for 20 min. After 20 min, the cells were washed-out and new fresh medium containing or not the compound was added for 48 h additional time. CR777 (1, 10, 100 pM, 1, 10, 100 nM, 1, 10 μM) was solved and diluted in culture medium and then pre-incubated with primary motor neurons for 1 hour before the glutamate application.

The following conditions were assessed:
Control
+ glutamate (5 μM 20 mn then 48 h)
+ glutamate (5 μM 20 mn then 48 h)+CR777 1 pmol/L
+ glutamate (5 μM 20 mn then 48 h)+CR777 10 pmol/L
+ glutamate (5 μM 20 mn then 48 h)+CR777 100 pmol/L
+ glutamate (5 μM 20 mn then 48 h)+CR777 1 nmol/L
+ glutamate (5 μM 20 mn then 48 h)+CR777 10 nmol/L
+ glutamate (5 μM 20 mn then 48 h)+CR777 100 nmol/L
+ glutamate (5 μM 20 mn then 48 h)+CR777 1 μmol/L
+ glutamate (5 μM 20 mn then 48 h)+CR777 10 μmol/L c) Immunostaining of Cells 48 hours after intoxication, the cell culture supernatants were taken off and the SC motor neurons were fixed by a cold solution of ethanol (95%, Sigma, batch: SZBD3080V) and acetic acid (5%, Sigma, Batch: SZBD1760V) for 5 min. After permeabilization with 0.1% of saponin, cells were incubated for 2 hours with an anti microtubule-associated-protein 2 monoclonal antibody (MAP-2; Sigma, batch: (063M4802) at dilution of 1/400 in PBS containing 1% foetal calf serum and 0.1% of saponin. This antibody specifically stains cell bodies of neurons, allowing study of neuron survival in the culture.

This antibody was revealed with Alexa Fluor 488 goat anti-mouse IgG (Molecular probe, batch: 1613346) at the dilution of 1/400 in PBS containing 1% foetal calf serum and 0.1% of saponin for 1 hour at room temperature.

d) Results

For each condition, 6 wells were assessed, 30 pictures per well were taken using ImageXpress (Molecular Devices) with 20× magnification, to assess motor neuron survival (MAP-2). Analysis of picture was done using Custom Module Editor (Molecular Devices). Results were expressed in terms of mean survival neuron, labeled for MAP-2. Data were expressed in percentage of control conditions (no intoxication, no glutamate=100%) in order to express the glutamate injury. All values were expressed as mean+/− SEM (s.e.mean) of the culture (n=6 wells per condition per culture). Graphs and statistical analyses are made on the different conditions (ANOVA followed by PLSD Fisher's test when allowed, using Statview software version 5.0).

Figure 11:
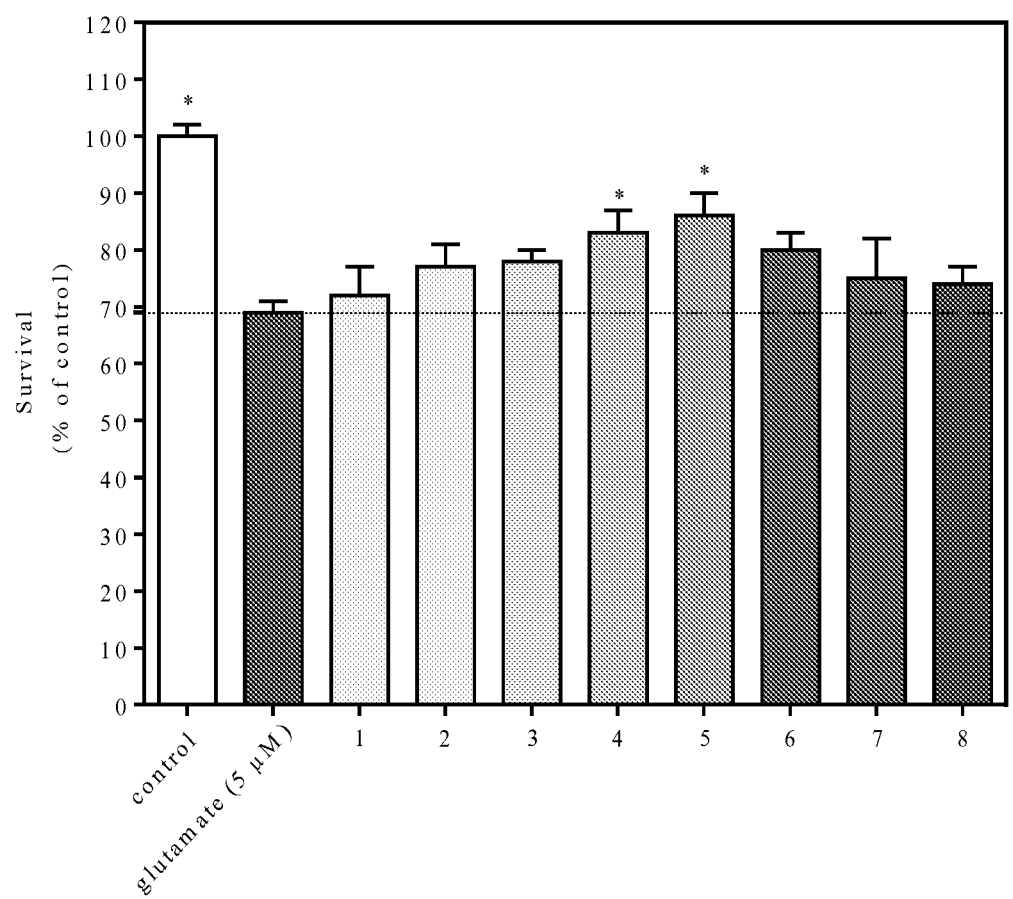

Glutamate (5 μM for 20 min) induced a significant motor neuron death (>30%). CR777 added 1 h before the glutamate application, displayed a moderate and significant protective effect of motor neuron between 1 nM and 10 nM concentration. (FIG. 11).

The invention claimed is:

1. A compound of formula (I)

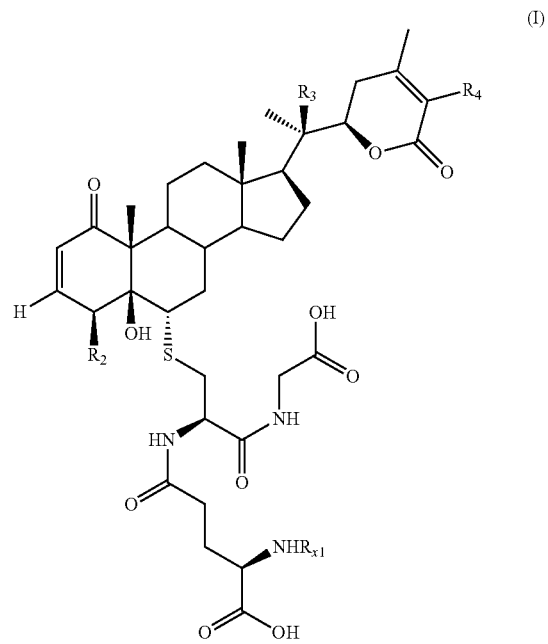

(I)

in which
$R_2$ is H, OH, F, Cl, Br, I, $(CH_2)n\text{-}CH_3$, with n=2, 4 or 6, a glucopyranose or a glucofuranose;
$R_3$ is H, OH, $CH_2OH$ or a glucofuranose;
$R_4$ is H, OH, $CH_3$, $CH_2OH$, a glucofuranose, a phenyl group, a naphthyl group, a phenyl group substituted by one halide X, or a naphthyl group substituted by one halide X, wherein X is F, Cl, Br or I; and
$R_{X1}$ is H or an amino acid chosen among tryptophan, lysine, methionine, phenylalanine, threonine, valine, leucine, isoleucine, arginine or histidine.

2. The compound according to claim 1 in which
$R_2$ is H, OH, F, Cl, Br, or I;
$R_3$ is H, OH or $CH_2OH$;
$R_4$ is H, OH, $CH_3$, $CH_2OH$; and
$R_{X1}$ is H or an amino acid chosen among tryptophan, lysine, methionine, phenylalanine, threonine, valine, leucine, isoleucine, arginine or histidine.

3. The compound according to claim 1 in which
$R_2$ is OH;
$R_3$ is H;
$R_4$ is $CH_2OH$; and
$R_{X1}$ is H.

4. A method of synthesis of the compound of formula (I) according to claim 1, comprising two successive stages (a1) and (a2):
(a1) the reaction between compound of formula (II) in which the substituent $R_1$ is H, OH, F, Cl, Br, I, or $(CH_2)n\text{-}CH_3$, with n=2, 4 or 6; and $R_2$, $R_3$, and $R_4$ have the same meaning as in formula (I),

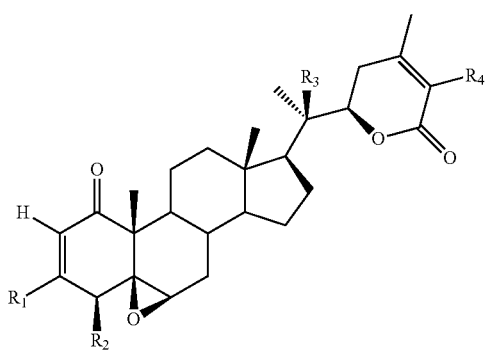

and the compound of formula (III) in which the substituent $R_{X1}$ has the same meaning as in formula (I)

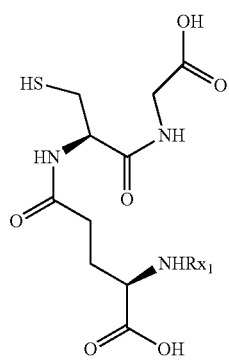

to obtain the compound of formula (IV)

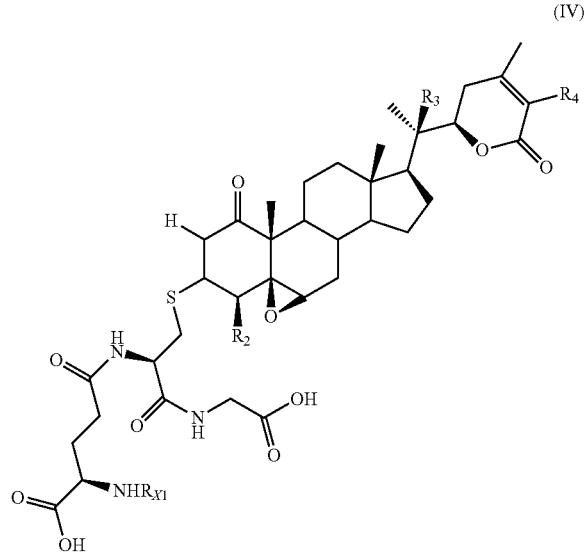

in which the substituents $R_2$, $R_3$, $R_4$, and $R_{X1}$ have the same meaning as in formula (I), and (a2) the reaction between compound of formula (IV) with the compound of formula (III) to obtain the compound of formula (I).

5. The method of synthesis according to claim 4, in which the stages (a1) and (a2) are in the presence of a solvent.

6. The method of synthesis according to claim 5, in which the solvent is tetrahydrofuran and/or water.

7. A method of increasing a number of myelin-associated glycoprotein (MAG) positive cells, and increasing a precursor cell of oligodendrocytes (OPC) and oligodendrocytes (OL), the method comprising administering to a patient, in need thereof, a therapeutic amount of a compound according to claim 1.

8. The method of claim 7, wherein the patient is suffering from an amyloid-related disease, wherein the amyloid disease is Alzheimer's disease, cerebral amyloid angiopathy, inclusion body myositis, macular degeneration, or Down's syndrome.

9. The method according to claim 8, wherein amyloid fibril formation or deposition, neurodegeneration, or cellular toxicity is reduced or inhibited.

10. The method of claim 7, wherein the patient is suffering from a demyelinating disease, wherein the demyelinating disease is chosen from multiple sclerosis, acute disseminated encephalomyelitis, adrenoleukodystrophy, adrenomyeloneuropathy, Leber's Hereditary Optic Atrophy, Human T-Lymphotropic Virus (HTLV)-associated Myelopathy and to demyelination of the Peripheral Nervous System (PNS).

11. The method of claim 7, wherein the patient is suffering from a neuromuscular disease, wherein the neuromuscular disease is chosen from MN disease, ALS, PBP, PMA, PLS, SMA, Kennedy's disease, PPS, PPMA, MMN, MMA, paraneoplastic motor neuron disease, LEMS, MG and botulism.

12. The method of claim 7, wherein the patient is suffering from an α-synucleinopathy, wherein the α-synucleinopathy is chosen from Parkinson disease, dementia with Lewy bodies, multiple system atrophy, Lewy bodies dysphagia, neurodegeneration with brain iron accumulation type I and pure autonomic failure.

13. The method according to claim 7, wherein the therapeutic compound is administered orally or parenterally.

14. The method according claim 7, wherein said therapeutic compound is administered in a pharmaceutically acceptable vehicle.

* * * * *